United States Patent
Harris et al.

(10) Patent No.: US 10,548,673 B2
(45) Date of Patent: Feb. 4, 2020

(54) SURGICAL TOOL WITH A DISPLAY

(71) Applicant: Ethicon Endo-Surgery, LLC, Guaynabo, PR (US)

(72) Inventors: Jason L. Harris, Lebanon, OH (US); Frederick E. Shelton, IV, Hillsboro, OH (US); Nichole Y. Kwee, Cincinnati, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 601 days.

(21) Appl. No.: 15/237,712

(22) Filed: Aug. 16, 2016

(65) Prior Publication Data
US 2018/0049819 A1    Feb. 22, 2018

(51) Int. Cl.
*A61B 34/30* (2016.01)
*A61B 34/00* (2016.01)
(Continued)

(52) U.S. Cl.
CPC ............ *A61B 34/30* (2016.02); *A61B 17/064* (2013.01); *A61B 17/068* (2013.01); *A61B 34/25* (2016.02);
(Continued)

(58) Field of Classification Search
CPC ... A61B 17/115; A61B 17/064; A61B 17/068; A61B 17/07207; A61B 17/07292;
(Continued)

(56) References Cited

U.S. PATENT DOCUMENTS

| 5,307,976 A | 5/1994 | Olson et al. |
| 5,308,358 A | 5/1994 | Bond et al. |

(Continued)

FOREIGN PATENT DOCUMENTS

EP    2792308 A2    10/2014

OTHER PUBLICATIONS

International Search Report and Written Opinion for PCT/US2017/046455 dated Nov. 14, 2017 (14 pages).
(Continued)

*Primary Examiner* — Nathaniel C Chukwurah
(74) *Attorney, Agent, or Firm* — Mintz Levin Cohn Ferris Glovsky and Popeo, P.C.

(57) ABSTRACT

A surgical tool assembly is provided that is configured to be removably and replaceably attached to an electromechanical arm of a surgical robotic system that is capable of supplying electrical power to the surgical tool assembly. The tool assembly has a housing and an elongate shaft extending distally from the housing and having an end effector at a distal end thereof. The housing has a display configured to present information related to operation of the surgical tool assembly, and one or more controls. The end effector has opposed jaws that are movable between open and closed positions, and at least one of the jaws supports a removable and replaceable staple cartridge assembly. The controls are configured to accept user input comprising instructions to the surgical robotic system, including an instruction to open the jaws of the end effector, which can then be loaded with another staple cartridge assembly.

10 Claims, 21 Drawing Sheets

(51) Int. Cl.
  *A61B 17/068* (2006.01)
  *A61B 34/37* (2016.01)
  *A61B 17/064* (2006.01)
  *A61B 17/00* (2006.01)
  *A61B 17/072* (2006.01)

(52) U.S. Cl.
  CPC .... *A61B 34/37* (2016.02); *A61B 2017/00199* (2013.01); *A61B 2017/00473* (2013.01); *A61B 2017/07271* (2013.01)

(58) Field of Classification Search
  CPC ......... A61B 34/30; A61B 34/10; A61B 34/25; A61B 34/37
  USPC ..................................... 227/176.1, 19, 180.1
  See application file for complete search history.

(56) References Cited

U.S. PATENT DOCUMENTS

| | | | |
|---|---|---|---|
| 5,312,023 | A | 5/1994 | Green et al. |
| 5,318,221 | A | 6/1994 | Green et al. |
| 5,484,451 | A | 1/1996 | Akopov et al. |
| 5,487,500 | A | 1/1996 | Knodel et al. |
| 5,782,396 | A | 7/1998 | Mastri et al. |
| 8,114,345 | B2 | 2/2012 | Dlugos, Jr. et al. |
| 8,882,792 | B2 | 11/2014 | Dietz et al. |
| 8,915,842 | B2 | 12/2014 | Weisenburgh, II et al. |
| 8,931,682 | B2 | 1/2015 | Timm et al. |
| 8,945,098 | B2 | 2/2015 | Seibold et al. |
| 2005/0127131 | A1 | 6/2005 | Mastri et al. |
| 2005/0131390 | A1* | 6/2005 | Heinrich ............ A61B 17/0469 606/1 |
| 2008/0021440 | A1* | 1/2008 | Solomon ................ B25J 9/1045 606/1 |
| 2008/0081948 | A1 | 4/2008 | Weisenburgh et al. |
| 2009/0202387 | A1 | 8/2009 | Dlugos, Jr. et al. |
| 2010/0131005 | A1 | 5/2010 | Conlon |
| 2011/0118709 | A1 | 5/2011 | Burbank |
| 2011/0118778 | A1 | 5/2011 | Burbank |
| 2012/0298719 | A1 | 11/2012 | Shelton, IV et al. |
| 2013/0012959 | A1 | 1/2013 | Jinno |
| 2013/0098970 | A1 | 4/2013 | Racenet et al. |
| 2013/0168431 | A1* | 7/2013 | Zemlok ............ A61B 17/07207 227/175.1 |
| 2013/0211397 | A1* | 8/2013 | Parihar .................. A61B 18/18 606/33 |
| 2013/0214025 | A1* | 8/2013 | Zemlok ................ A61B 17/068 227/175.1 |
| 2013/0282052 | A1 | 10/2013 | Aranyi et al. |
| 2014/0005662 | A1 | 1/2014 | Shelton, IV |
| 2014/0005678 | A1 | 1/2014 | Shelton et al. |
| 2014/0005718 | A1 | 1/2014 | Shelton, IV et al. |
| 2014/0257252 | A1 | 9/2014 | Ishida et al. |
| 2014/0257333 | A1 | 9/2014 | Blumenkranz |
| 2014/0358163 | A1 | 12/2014 | Farin et al. |
| 2015/0272575 | A1 | 10/2015 | Leimbach |
| 2015/0272603 | A1 | 10/2015 | Shelton, IV et al. |
| 2018/0049737 | A1 | 2/2018 | Swayze et al. |
| 2018/0146960 | A1 | 5/2018 | Shelton et al. |
| 2018/0168589 | A1 | 6/2018 | Swayze et al. |
| 2019/0125464 | A1 | 5/2019 | Remm |

OTHER PUBLICATIONS

Correlated Solutions, "Principle of Digital Image Correlation," 2013 (http://correlatedsolutions.com/digital-image-correlation/).
U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques" filed Jun. 9, 2016.

* cited by examiner

SURGICAL TOOL WITH A DISPLAY

FIELD

Methods and devices are provided for robotic surgery, and in particular for controlling robotic tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In one aspect, a robotic surgical device is provided that in some embodiments includes a surgical tool assembly configured to be removably and replaceably attached to an electromechanical arm of a surgical robotic system that is capable of supplying electrical power to the surgical tool assembly. The surgical tool assembly has a housing, an elongate shaft extending distally from the housing and having an end effector at a distal end thereof, the end effector having opposed jaws that are movable between open and closed positions with at least one of the jaws comprising a removable and replaceable staple cartridge assembly, a display on the housing, the display having an interface configured to present user information related to operation of the surgical tool assembly, and one or more controls formed on the housing and configured to accept user input including at least one instruction to the surgical robotic system, the at least one instruction comprising an instruction to open the jaws.

The robotic surgical device can vary in a number of different ways. For example, in some embodiments, the surgical tool assembly can include a member configured to move distally and proximally within at least a portion of the end effector to open and close the jaws. In such embodiments, the instruction to open the jaws includes an instruction to cause the member to automatically move proximally to thereby open the jaws. As another example, the interface can be a touch screen interface.

The at least one instruction that can be accepted by one or more controls can include an instruction to cause the surgical tool assembly to be removed from a surgical access instrument. The one or more controls can vary in many different ways. For example, the one or more controls can include at least one button.

The information related to operation of the surgical tool assembly can include information about an operational status of the surgical tool assembly. Such information can include an indication that the staple cartridge assembly has been removed from the end effector when the staple cartridge assembly is absent from the end effector. The information can also include at least one of an indication that the cartridge assembly is required to be replaced, an indication of whether the cartridge assembly has been installed correctly or incorrectly, instructions for reloading the end effector, instructions for operating the surgical tool assembly, and instructions for resolving at least one error in operation of the end effector.

In some embodiments, the at least one of the jaws is the replaceable and removable staple cartridge assembly and the at least one instruction to the surgical robotic system comprises an instruction to remove the at least one of the jaws from the end effector.

The elongate shaft can include a proximal portion and a distal portion having the end effector, the distal portion being removably and replaceably coupled to the proximal portion.

In another aspect, a method is provided that in some embodiments includes providing a surgical tool assembly configured to be removably and replaceably attached to an electromechanical arm of a surgical robotic system that is capable of supplying electrical power to the surgical tool assembly. The surgical tool assembly has a housing having a display and one or more controls, and an elongate shaft extending distally from the housing and having an end effector at a distal end thereof, the end effector having opposed jaws that are movable between open and closed positions with at least one of the jaws comprising a removable and replaceable staple cartridge assembly. The method further includes displaying on the display information related to operation of the surgical tool assembly, and receiving, via the one or more controls, user input comprising at least one instruction to the surgical robotic system, the at least one instruction comprising an instruction to open the jaws.

The method can vary in many different ways. For example, the surgical tool assembly can include a member configured to move distally and proximally within at least a portion of the end effector to open and close the jaws, the instruction to open the jaws can include an instruction to cause the member to automatically move proximally to thereby open the jaws. The one or more controls can include at least one button.

The at least one instruction to the surgical robotic system can include an instruction to cause the member to automatically move distally to thereby close the jaws. In some embodiments, the at least one instruction can further include an instruction to cause the surgical tool assembly to be removed from a surgical access instrument.

In some embodiments, the method further includes, after the removable and replaceable staple cartridge assembly has been replaced with another removable and replaceable staple cartridge assembly, receiving an instruction to close the jaws.

The information related to operation of the surgical tool assembly can include information about an operational status of the surgical tool assembly. Such information can include an indication that the cartridge assembly has been removed from the end effector when the cartridge assembly is absent from the end effector. The information can also include at least one of an indication that the cartridge assembly is required to be replaced, an indication of whether the cartridge assembly has been installed correctly or incorrectly, instructions for reloading the end effector, instructions for operating the surgical tool assembly, and instructions for resolving at least one error in operation of the end effector.

In some embodiments, the at least one of the jaws is the replaceable and removable staple cartridge assembly. In some embodiments, the elongate shaft includes a proximal portion and a distal portion having the end effector, the distal portion being removably and replaceably coupled to the proximal portion.

BRIEF DESCRIPTION OF THE DRAWINGS

The present disclosure will be more fully understood from the following detailed description taken in conjunction with the accompanying drawings, in which.

DETAILED DESCRIPTION

Figure 1:
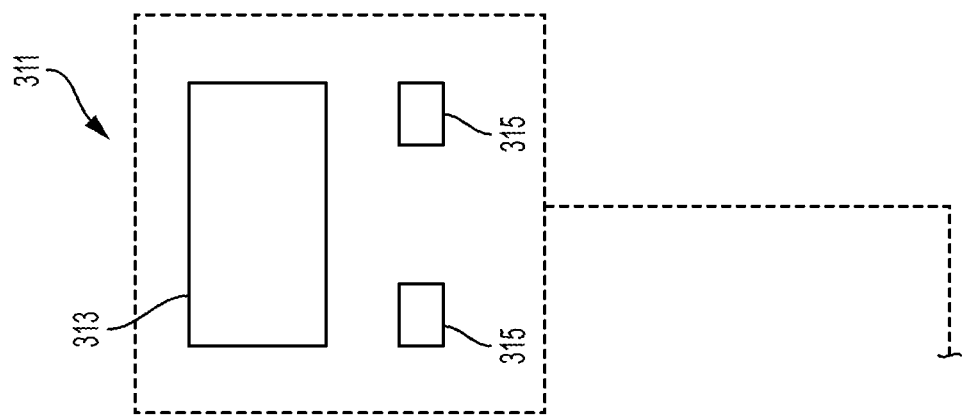
FIG. 1 is a perspective view of an embodiment of a surgical robotic system.
Figure 1:
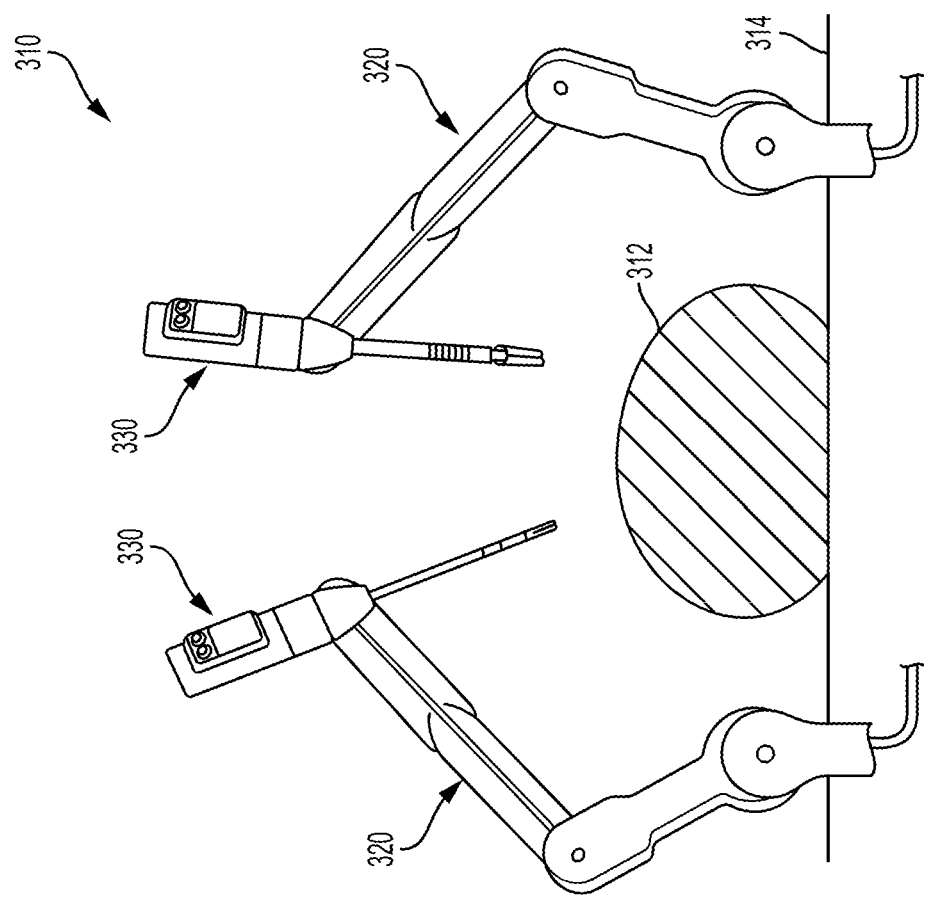

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, techniques are provided for controlling an end effector of a surgical tool assembly removably and replaceably attached to an electromechanical arm of a surgical robotic system that is capable of supplying electrical power to the surgical tool assembly. Specifically, the described techniques allow controlling the opening and closing of jaws of the end effector using a display. The jaws are configured to be opened for reloading a removable and replaceable staple cartridge assembly supported by the end effector. The surgical tool assembly includes a housing having a display that has an interface configured to present user information related to operation of the surgical tool assembly. The housing also has formed thereon one or more controls (e.g., buttons or other control elements) configured to accept user input comprising at least one instruction to the surgical robotic system. The at least one instruction includes an instruction to withdraw the end effector from a surgical access instrument (e.g., a trocar) and an instruction to open the jaws of the end effector.

Techniques are also provided for controlling a surgical tool assembly configured to be removably and replaceably attached to an electromechanical arm of a surgical robotic system that is capable of supplying electrical power to the surgical tool when the surgical tool is attached to the electromechanical arm. Specifically, the surgical tool assembly is controlled manually, via an actuator on an elongate shaft with an end effector at a distal end thereof having opposed jaws that are movable between open and closed positions, to open and close jaws of the end effector. The staple cartridge assembly can be removably seated by a cartridge body (e.g., by a cartridge channel), or the entire jaw can be a removable and replaceable staple cartridge assembly. The surgical tool includes a member (e.g., an I-beam, a driver shaft, etc.) configured to move distally and proximally within at least a portion of the end effector to open and close the jaws, and the actuator disposed on the shaft and configured to be manually moved from a first position to a second position to cause the member to move proximally to thereby open the jaws when the surgical tool is in a mode in which it is not deriving electrical power from the surgical robotic system. In this way, the jaws can be opened manually a removable and replaceable staple cartridge assembly supported by one of the jaws can be replaced with another removable and replaceable staple cartridge assembly.

Robotic Surgical Systems

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Robotic System

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

Figure 3:
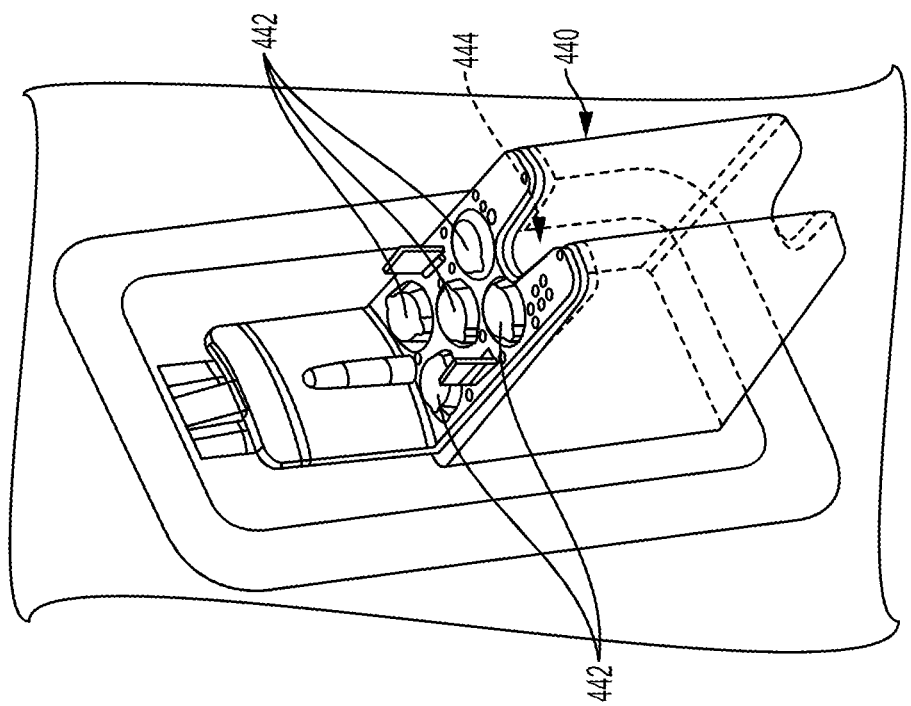
FIG. 3 illustrates the tool driver of FIG. 2 in more detail.

The patient-side portion can also have a variety of configurations. As depicted in FIG. 3, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 3). Alternatively, the patient-side portion 310 can include a single assembly that includes one or more robotic arms 320 extending therefrom.

Figure 2:
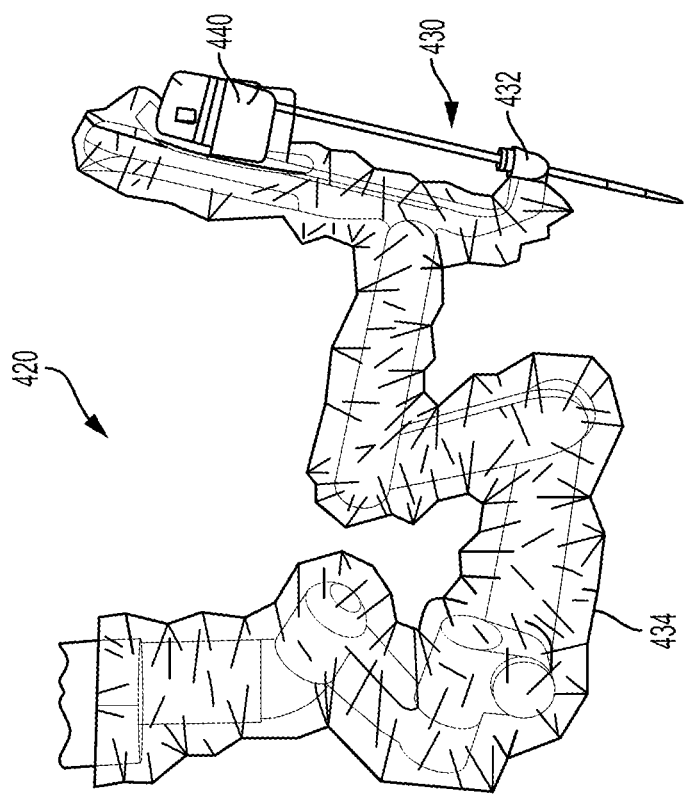
FIG. 2 illustrates an embodiment of a robotic arm and a tool assembly releasably coupled to the robotic arm.
Figure 9:
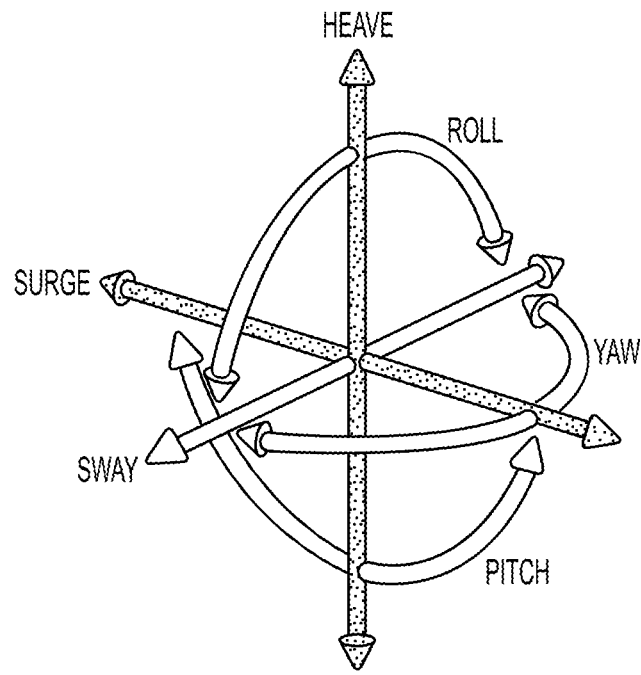
FIG. 9 illustrates movement and rotation along one of the three axes in a Cartesian frame.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, as illustrated in FIG. 9, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 (shown in FIG. 4) can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile statical field.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
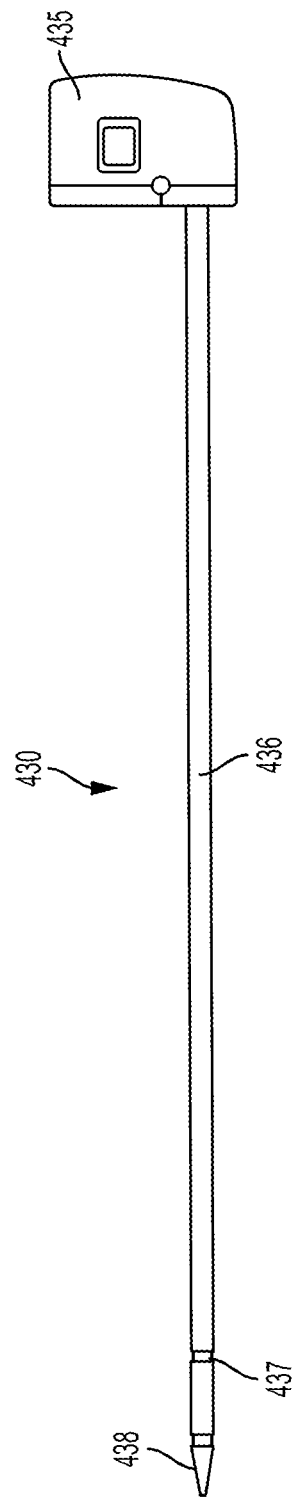
FIG. 4 illustrates the tool assembly uncoupled from the robotic arm.

FIG. 4 illustrates the tool assembly 430 uncoupled from the robotic arm 420. The tool assembly 430 includes a puck or housing 435 coupled to a proximal end of a shaft 436 and an end effector 438 coupled to a distal end of the shaft 436. The housing 435 can include coupling features that assist with releasably coupling the housing 435 to the tool driver 440 of the robotic arm 420. The housing 435 can include gears and/or actuators that can be actuated by the one or more motors 442 in the driver 440, as will be described in greater detail below. The gears and/or actuators in the housing 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the housing 435, or it can be releasably coupled to the puck 435 such that the shaft 436 can be interchangeable with other shafts. This can allow a single housing 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device an endoscope or ultrasound probe), or a combined device that includes a combination of two or more various tools.

Figure 5:
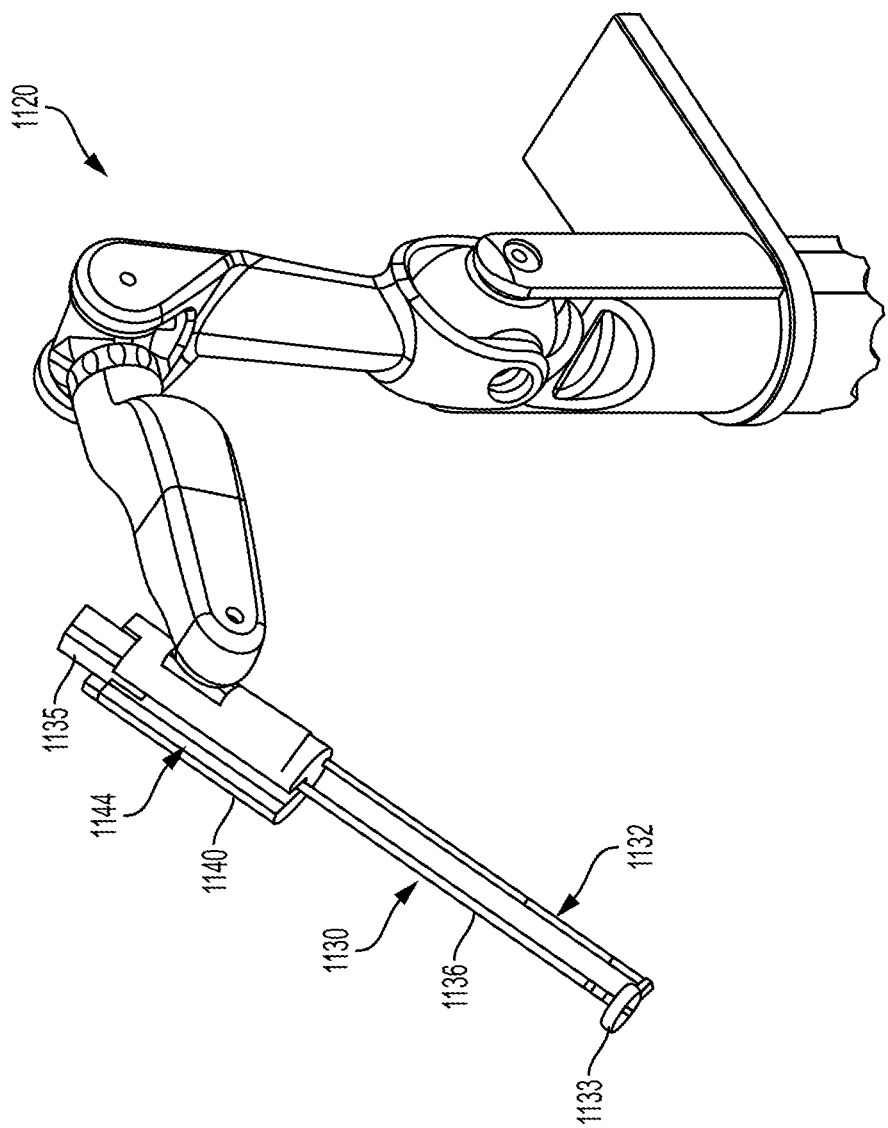
FIG. 5 illustrates an embodiment of the robotic arm of FIG. 1 having an embodiment of a tool assembly releasably coupled to the robotic arm.

FIG. 5 illustrates an embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the rob 1120, which can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature 1133 (e.g., a ring) of the movable tool guide 1130 and into a patient.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 6:
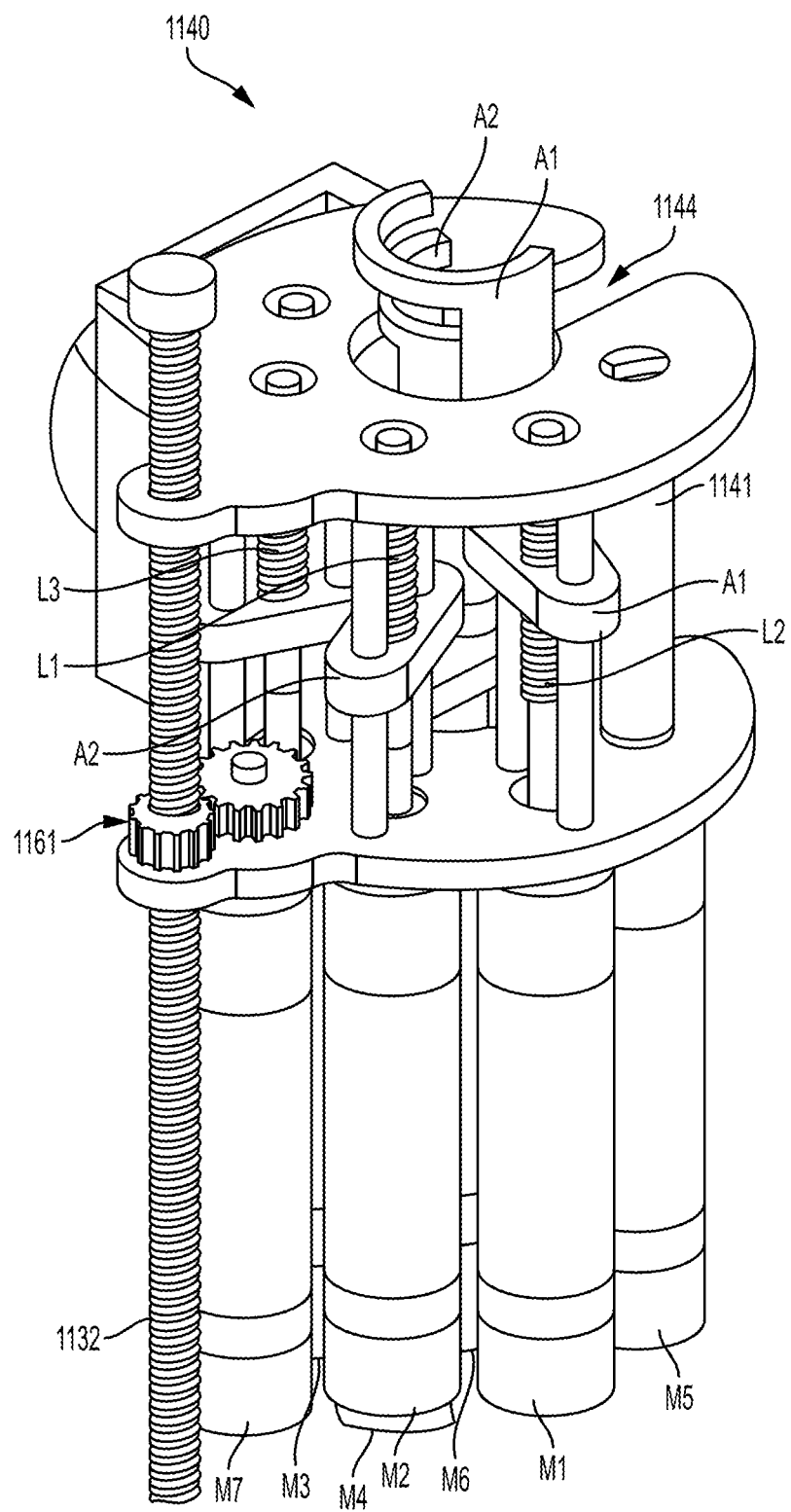
FIG. 6 illustrates an embodiment of a tool driver.

FIG. 6 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 6). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 7:
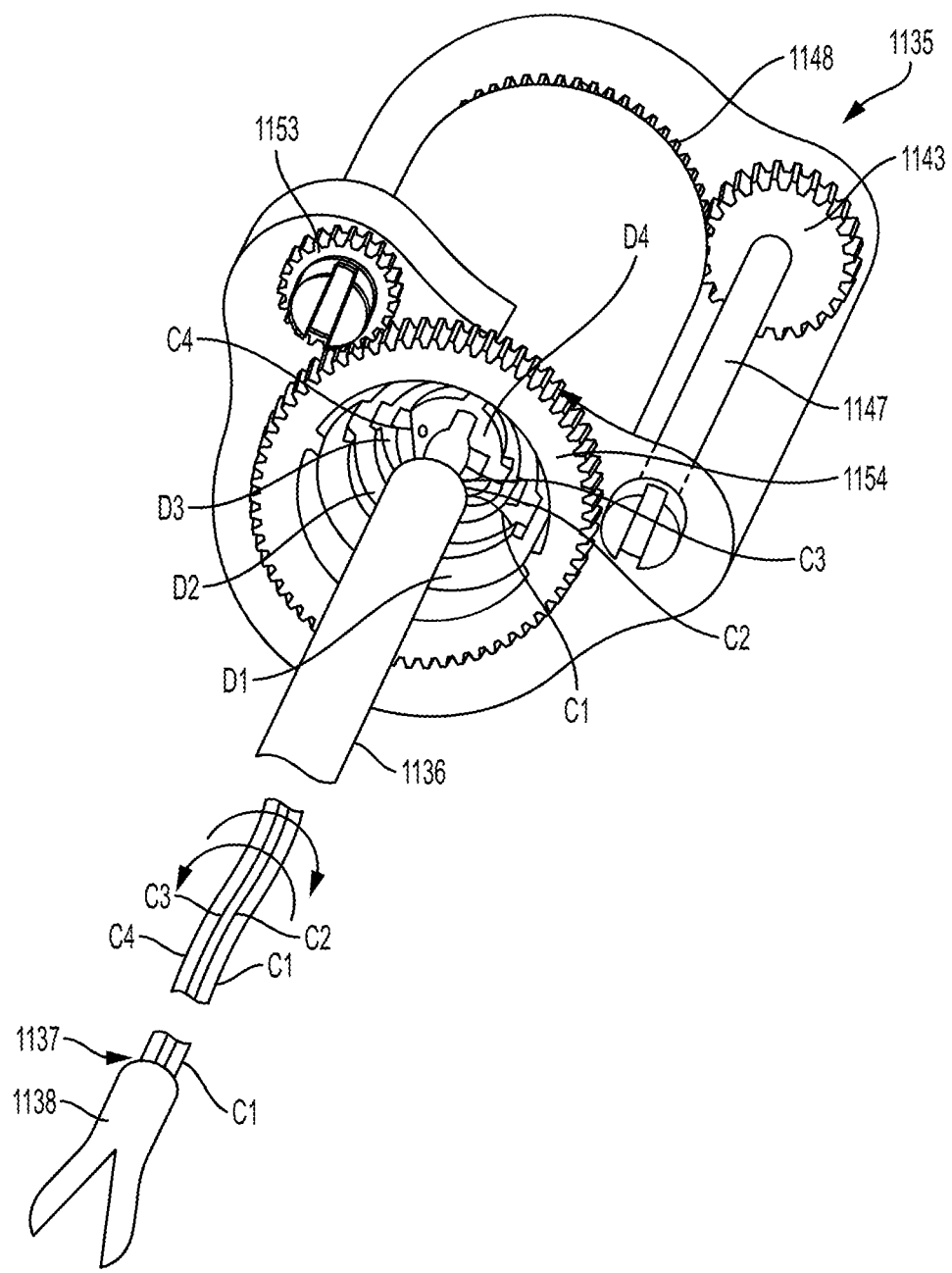
FIG. 7 illustrates a portion of a puck actuation assembly contained within a housing.

As shown in FIGS. 5 and 7, the tool assembly 1130 includes a puck or housing 1135 coupled to a proximal end of a shaft 1136 and an end effector 1138 coupled to a distal end of the shaft 1136. The housing 1135 can include coupling features that assist with releasably coupling the puck 1135 to the tool driver 1140 of the robotic arm 1120. The housing 1135 can include driving members (e.g., gears, cables, and/or drivers) that can be directly or indirectly actuated by the one or more motors M1-M5, as will be described in greater detail below. The driving members in the housing 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the housing 1135 such that the shaft 1136 can be interchangeable with other shafts. This can allow a single housing 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

FIG. 7 illustrates a part of a housing actuation assembly contained within the housing 1135. As shown in FIG. 7, the housing 1135 includes at least one driving member (e.g., four driving members D1, D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

Figure 8:
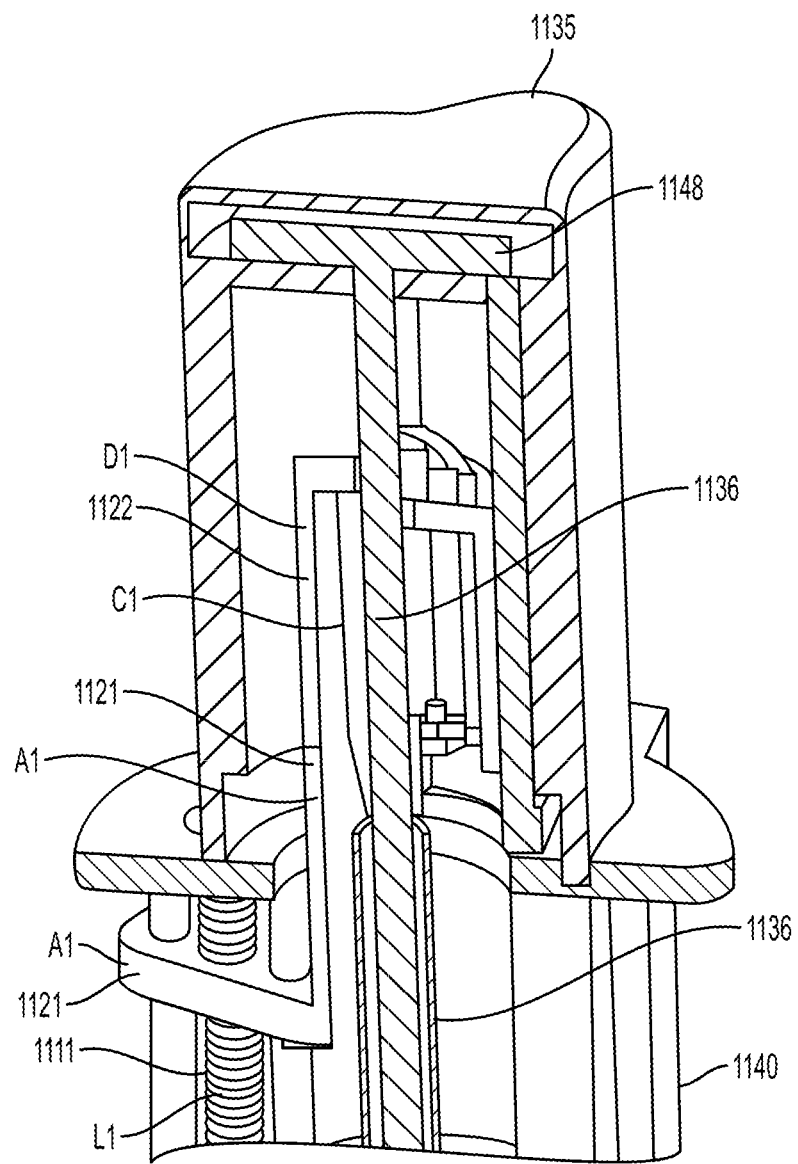
FIG. 8 illustrates an embodiment of a housing coupled to a driver with actuators extending from the driver into the puck and engaging driving member.

FIG. 8 illustrates the housing 1135 coupled to the driver 1140 with the actuators extending from the driver 1140 into the puck 1135 and engaging the driving members. For example, motor M1 can cause lead screw L1 to rotate thereby causing actuator A1, which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the housing 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first housing shaft 1147 having a first housing gear 1143 coupled to a distal end of the first puck shaft 1147. Rotation of the first driver shaft 1141 thereby causes the first housing shaft 1147 and first housing gear 1143 to rotate. The first housing gear 1143 is engaged with a first shaft rotation gear 1148 that is caused to rotate as a result of the first housing gear 1143 rotating. The first shaft rotation gear 1148 is operatively coupled to the shaft 1136 of the tool assembly 1130 and can thereby cause rotation of the shaft 1136 and/or end effector 1138. Motor M6 can cause a second driver shaft to rotate, which is operatively coupled to a second puck gear 1153. The second housing gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 9, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 10:
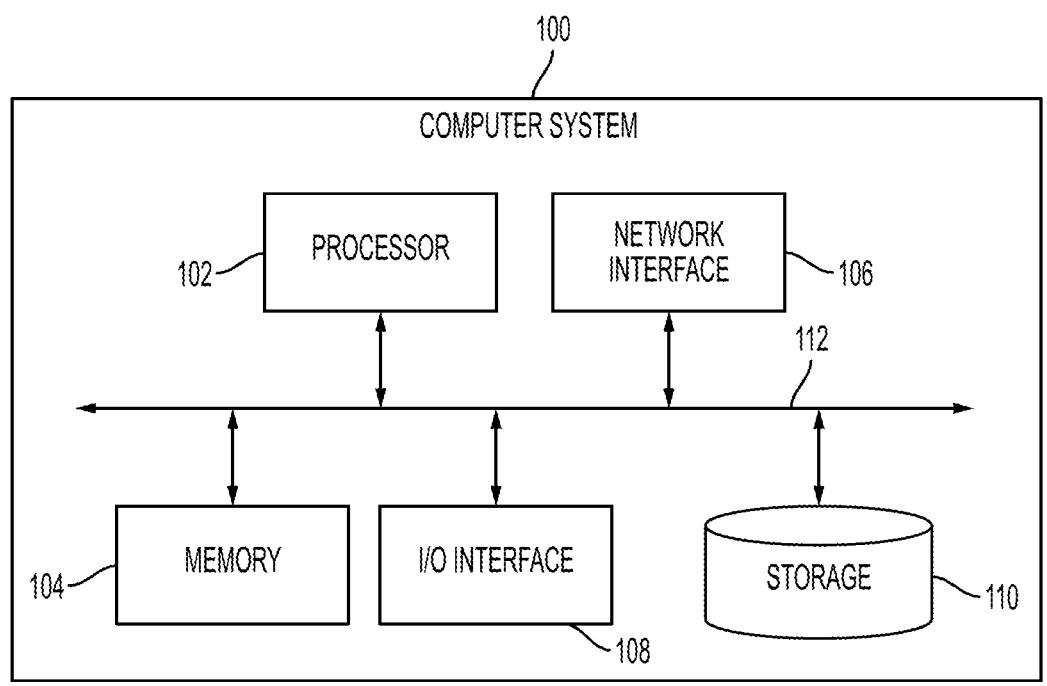
FIG. 10 illustrates one exemplary embodiment of a computer system having one or more features consistent with the present description.

FIG. 10 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 10 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Figure 11:
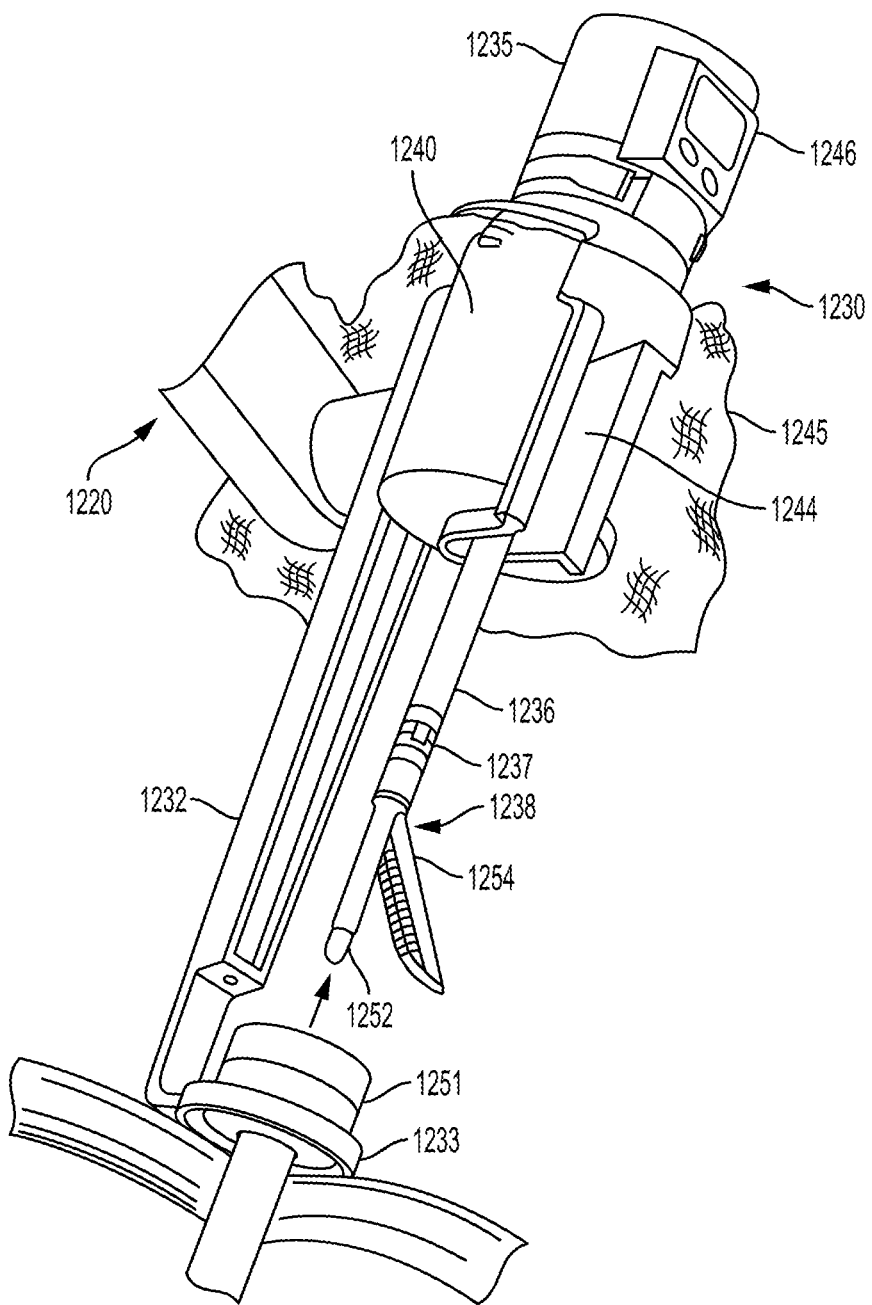
FIG. 11 is a perspective view of an embodiment of a portion of a surgical robotic system.

In some embodiments, a surgical robotic system can include a surgical tool that is releasably coupled to a robotic arm. The surgical tool can include a housing coupled to a proximal end of an elongate instrument shaft and an end effector coupled to a distal end of the shaft. FIG. 11 illustrates an embodiment of such robotic arm 1220 and a surgical tool assembly 1230 releasably coupled to the robotic arm 1220. The robotic arm 1220 can support and move the associated surgical tool assembly 1130 along one or more mechanical degrees of freedom (e.g., all six Cartesian degrees of freedom, five or fewer Cartesian degrees of freedom, etc.).

The robotic arm 1220 includes a tool driver 1240 at a distal end of the robotic arm 1220, which can assist with controlling features associated with the surgical tool assembly 1230. As shown in FIG. 11, the robotic arm 1220 also includes a tool guide 1232 that couples to a trocar 1251. The trocar 1251, which can have any suitable configuration, can be reversibly mated to a distal end feature 1233 (e.g., a ring or other feature) of the tool guide 1232. The tool guide 1232 holds the trocar 1251 to allow the shaft of the surgical tool assembly 1230, which extends generally parallel to a threaded shaft of the tool guide 1232, to be advanced through and retracted from the trocar.

While the tool driver 1240 is not shown in detail, it generally includes one or more motors that control a variety of movements and actions associated with the tool assembly 1230. Each motor can be configured to couple to a drive assembly in the tool driver to thereby cause movement of a corresponding actuator, which in turn actuates the end effector. For example, actuation of one of the motors can rotate one or more gear assemblies, which in turn can cause linear and/or rotational movement of at least one actuator (e.g., gears, cables) extending through the tool shaft. Each actuator can cause actuation of the end effector, e.g., clamping, rotating, articulation, etc.

As further shown in FIG. 11, the surgical tool assembly 1230 can be loaded from a top side of the driver 1240 with the shaft of the tool assembly 1230 being positioned in a shaft-receiving channel 1244 formed along the side of the driver 1240. The shaft-receiving channel 1244 allows the shaft, which extends along a central axis of the tool assembly 1230, to extend along a central axis of the driver 1240 when the tool assembly 1230 is coupled to the driver 1240. In other embodiments, the shaft can extend through on opening in the tool driver 1240, or the two components can mate in various other configurations.

As shown in FIG. 11, the surgical tool assembly 1230 includes a housing 1235 coupled to a proximal end of an elongate shaft 1236 that extends distally from the housing 1235. The tool assembly 1230 also includes an end effector 1238 coupled to a distal end of the shaft 1236. In some embodiments, as in the example illustrated, the surgical tool assembly 1230 can include a sterile barrier (not shown). However, it should be appreciated that, in some embodiments, the sterile barrier may not be present.

The housing 1235 can have various configurations. In this example, as shown in FIG. 11, the housing 1235 can be generally cylindrical, though it can have other shapes. As also shown, the housing 1235 can include a display 1246 which is discussed in more detail below. In at least some embodiments, the housing 1235 can include coupling features that assist with releasably coupling the housing 1235 to the tool driver 1240 of the robotic arm 1220. The housing 1235 can include drivers (e.g., gears, shafts, cables etc.) that can be directly or indirectly actuated by the one or more motors in the tool driver. Each driving member in the housing 1235 can cause rotation or translation of an actuator (e.g., shaft, cable) extending through the elongate shaft and coupled to the end effector. Movement of the actuators can control the operation of various features associated with the end effector 1238 (e.g., clamping, firing, rotation, articulation, etc.), as well as control the movement of the shaft 1236 (e.g., rotation and/or articulation of the shaft).

The shaft 1736 can be releasably coupled to the housing 1235 such that the shaft 1736 can be interchangeable with other shafts. This can allow a single housing 1235 to be adaptable to various shafts 1236 having different end effectors 1238. The shaft 1236 can also include one or more joints or wrists 1237 that allow a part of the shaft 1236 or the end effector 1238 to rotate and/or articulate relative to the longitudinal axis of the shaft 1236. This can allow for fine movements and various angulation of the end effector 1238 relative to the longitudinal axis of the shaft 1236.

The end effector 1238 can have various different configurations. In the example illustrated, as shown in FIG. 11, the end effector 1238 has opposed first and second jaws 1250, 1252 that are movable between open and closed positions. At least one of the jaws can include a removable and replaceable staple cartridge assembly. In this example, the first jaw 1250 can include a removable and replaceable staple cartridge assembly 1254, whereas the second jaw 1252 can be an anvil configured to approximate with respect to the first jaw 1250 having the cartridge assembly 1254. The first jaw 1250 can removably and replaceably seat the staple cartridge assembly 1254. Additionally or alternatively, the first jaw 1250 can be configured such that the entire jaw 1250 with the staple cartridge assembly 1254 is a removable and replaceable jaw.

As described above, an end effector of a surgical tool can have a removable and replaceable staple cartridge assembly. For example, as discussed above in connection with FIG. 11, at least one of the jaws of the end effector (e.g., a cartridge body) can seat the staple cartridge assembly. For example, one of the jaws can have a channel configured to removably and replaceably seat the staple cartridge assembly. The staple cartridge assembly holds staples configured to be applied by the end effector to seal tissue held by the jaws. When a replacement of the staple cartridge assembly is required (e.g., when the staple cartridge assembly is out of staples, or for other reasons), the staple cartridge assembly can be removed from the end effector and the end effector can be reloaded with a new staple cartridge assembly. Depending on a configuration of the end effector, the cartridge assembly can be removed from a jaw carrying the cartridge assembly (e.g., the first jaw 1250 in FIG. 11), or the entire removable and replaceable jaw can be removed and then replaced with another removable and replaceable jaw having a staple cartridge assembly.

Regardless of the specific configuration of the staple cartridge assembly and the way in which it is removably associated with the end effector of a surgical tool, for the staple cartridge assembly to be removed, the jaws of the end effector need to be open so that the end effector is properly accessible. Also, if the staple cartridge assembly is to be removed, a cutting element (e.g., a knife), if present, needs to be retracted proximally. Furthermore, to access the end effector for removal of the staple cartridge assembly, the surgical tool having the end effector needs to be retracted from a surgical access instrument. The surgical access instrument can be, for example, a trocar (e.g., the trocar 1251 in FIG. 11), that is inserted through an incision to form a pathway that provides access to a surgical site. The surgical access instrument is used to introduce the surgical tool (as well as other instruments) to the surgical site.

In some embodiments, to retract the surgical tool or at least a portion thereof (e.g., the end effector coupled to an elongate shaft of the tool) from the trocar, the tool should be placed in a mode (also referred to herein as a "first mode") in which it is not deriving electrical power from the surgical robotic system. For example, the tool can be disconnected from the tool driver, or supply of electrical power to the tool can be otherwise terminated. Thus, prior to retracting the surgical tool from the surgical access instrument, while the end effector coupled to an elongate shaft of the tool is still at least partially disposed within the trocar, the surgical tool is placed in such a mode. However, while the end effector is at least partially disposed within the trocar, its jaws are closed such that the end effector can fit within the inner opening of the trocar. In this way, when the power is not supplied to the tool and thus to the end effector, the end effector is "locked" in the closed-jaw configuration and it is retracted from the trocar with the jaws being closed. Thus, after the tool is retracted from the trocar, the end effector has its jaws closed and access to the cartridge assembly supported by the end effector is therefore prevented.

To overcome the above shortcoming, in some embodiments, a surgical tool can include an actuator disposed on the elongate shaft and configured to be manually moved from a first position to a second position to open the jaws when the surgical tool is in the first mode in which it is not deriving electrical power from the surgical robotic system. The surgical tool has a member that extends at least partially through the end effector and the shaft, the member being configured to move distally and proximally within at least a portion of the end effector to open and close the jaws. The actuator disposed on the shaft is configured to be manually moved from the first position to the second position to cause the member to move proximally to thereby open the jaws.

Accordingly, when the surgical tool is in the first mode, the actuator can be manually moved from the first position to the second position to cause the member to move proximally to open the jaws of the end effector. After the jaws of the end effector have been opened, a removable and replaceable staple cartridge assembly supported by at least one of the jaws can be replaced with another removable and replaceable staple cartridge assembly. The actuator can then be manually moved from the second position to the first position to cause the member to move distally to thereby close the jaws. After the jaws are closed, the surgical tool can be placed in the second mode in which it derives electrical power from the surgical robotic system.

Figure 12:
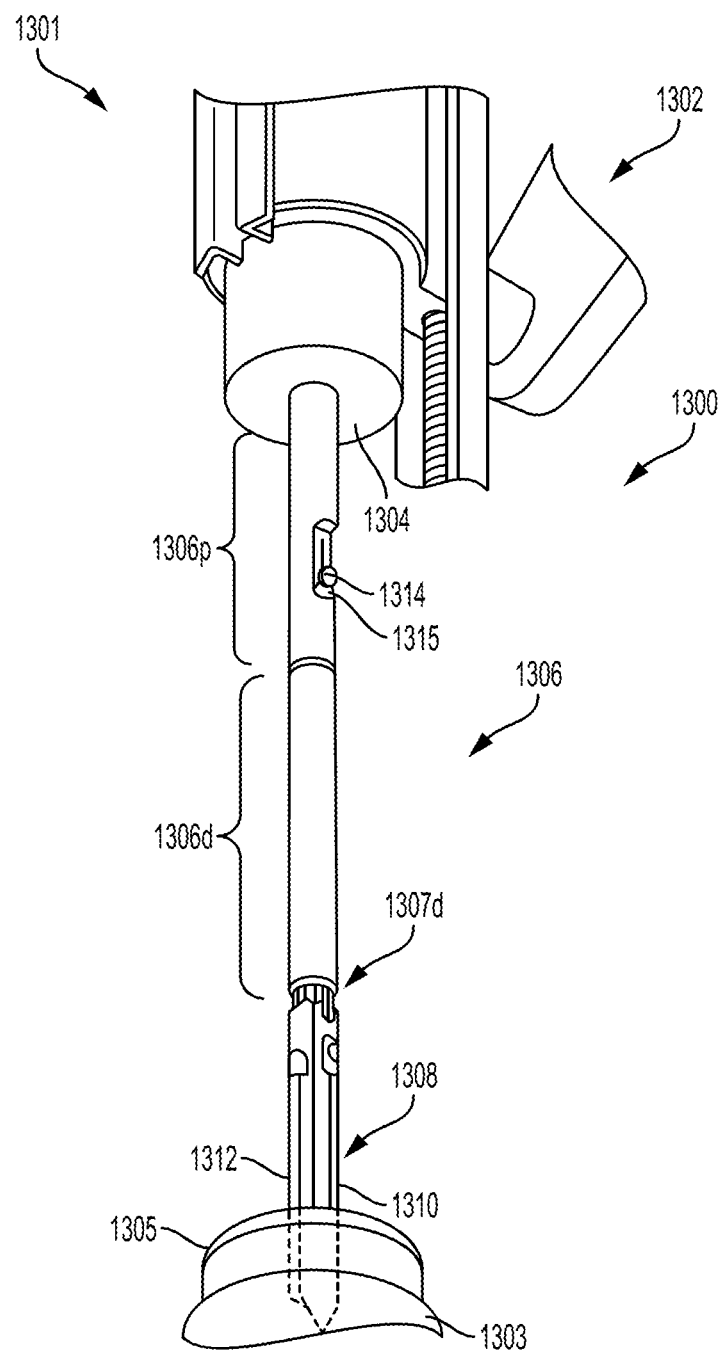
FIG. 12 is a perspective view of an embodiment of a surgical tool assembly in accordance with some embodiments.

FIG. 12 illustrates an example of a surgical tool assembly or surgical tool 1300 having an actuator in accordance with the described techniques. The surgical tool 1300, which can be part of a tool assembly 1301 of a surgical robotic system, is configured to be removably and replaceably attached to an electromechanical arm 1302 of a surgical robotic system that is capable of supplying electrical power to the surgical tool when the surgical tool is attached to the electromechanical arm. The electromechanical arm 1302 can have any suitable configuration, and only a portion of the arm 1302 is shown in FIG. 12. The surgical tool 1300 can be removably and replaceably coupled to the arm 1302 in any suitable way.

As shown in FIG. 12, the surgical tool 1300 has a housing 1304 and an elongate shaft 1306 extending distally from the housing 1304. The elongate shaft 1306 has, at a distal end 1307d thereof, an end effector 1308 having opposed first and second jaws 1310, 1312 that are movable between open and closed positions. The housing 1304 can be a tool driver that assists with controlling features associated with the surgical tool 1300. The elongate shaft 1306 can include a proximal portion 1306p and a distal portion 1306d having the end effector 1308. The distal portion 1306d can be removably and replaceably coupled to the proximal portion 1308p. In this way, the distal portion 1306d with the end effector 1308 can be replaced with another portion of an elongate shaft having an end effector coupled thereto. In such a configuration, the proximal portion 1306p of the end effector 1308 and at least a part of the tool driver can form an adapter configured to mate with various modular shaft assemblies such as, in this example, the distal portion 1306d with the end effector 1308. The tool driver can supply electrical power to a tool attachment including at least a portion of the shaft 1306 and the end effector 1308 when the tool attachment is attached to the tool driver. However, it should be appreciated that in some embodiments the elongate shaft 1306 may be formed as a single element such that its distal portion is not separable from its proximal portion.

In use, the tool assembly 1301 can be provided to a surgical site via a surgical access instrument, such as a trocar 1303, which can have any suitable configuration. The trocar 1303 can be reversibly mated to a distal end feature 1305 (e.g., a ring or other feature) of a tool guide (e.g., the tool guide 1232 in FIG. 11) or other feature.

Figure 13A:
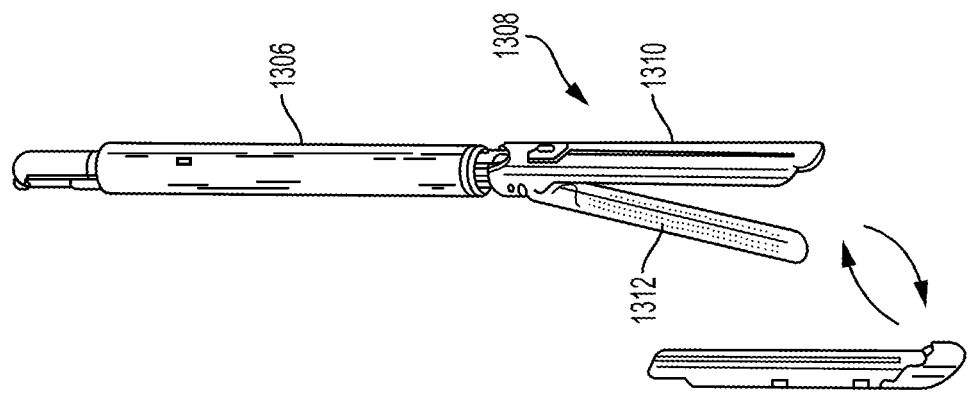
FIG. 13A illustrates a portion of the surgical tool assembly of FIG. 12, illustrating jaws of an end effector of the surgical tool assembly open.
Figure 13B:
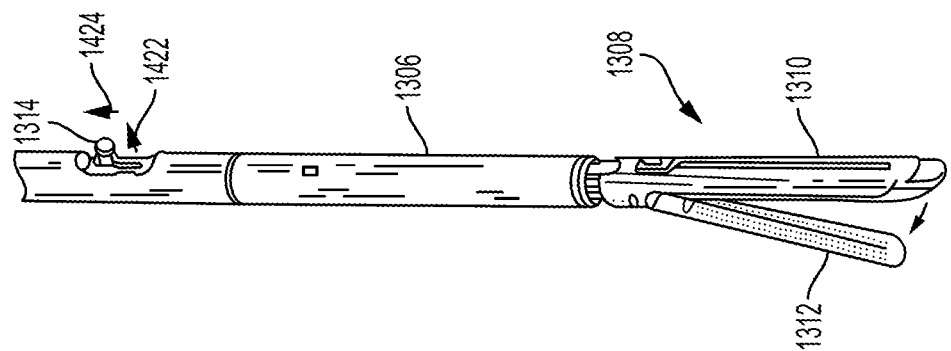
FIG. 13B illustrates the end effector of FIG. 13A, showing a staple cartridge assembly configured to be supported by the end effector.

Regardless of the specific configuration of the tool assembly 1301, as mentioned above, the surgical tool 1300 includes the end effector 1308 coupled to a distal end 1307d of the elongate shaft 1306. At least one of the opposed first and second jaws 1310, 1312 of the end effector 1308 can be removable and replaceable or can include a removable and replaceable staple cartridge assembly. Thus, as shown in FIGS. 13A and 13B which are discussed in more detail below, the first jaw 1310 can include a staple cartridge assembly 1311, whereas the second jaw 1312 can be an anvil. As shown in FIG. 12, when the end effector 1308 is at least partially inserted into the trocar 1303, the jaws 1310, 1312 are closed. To remove the surgical tool 1300 from the trocar 1303, the tool 1300 is placed in a mode in which it is not deriving electrical power from the surgical robotic system. For example, the surgical tool 1300 can be disconnected from the tool driver or other component supplying electrical power to the tool 1300. Supply of the electrical power to the tool 1300 is terminated while the jaws 1310, 1312 of the end effector 1308 are closed. In this way, the jaws 1310, 1312 are locked in the closed position. Thus, the tool 1300 is retracted from the trocar 1303 with the end effector's jaws in this closed position such that the staple cartridge assembly 1311 (FIG. 13B) is not accessible for removal.

In the illustrated embodiments, the surgical tool 1300 includes an actuator 1314 disposed on the elongate shaft 1306. The actuator 1314 is configured to be manually moved, within a slot 1315 formed in the elongate shaft 1306, from a first position to a second position to open the jaws 1310, 1312 when the surgical tool 1300 is in a mode in which it is not receiving electrical power from the surgical robotic system. In this way, the jaws 1310, 1312 of the end effector 1308 can be opened even if no electrical power is supplied to the surgical tool 1300. Thus, after the tool 1300 is retracted from a surgical access instrument (e.g., the trocar 1311) with the jaws 1310, 1312 closed, the actuator 1314 can be manually manipulated to cause the jaws 1310, 1312 to open.

Any suitable mechanism can be used to cause the jaws 1310, 1312 to open using the actuator 1314. The surgical tool 1300 also includes an elongate member 1400 (shown in FIGS. 14A-14C discussed in more detail below) extending through a least a portion of the length of the elongate shaft 1306 and configured to move distally and proximally within at least a portion of the end effector 1308 to open and close the jaws 1310, 1312. The member 1400 can be, for example, a drive member (e.g., a drive shaft), an I-beam compression member, an articulation cable, or any other element configured to move distally and proximally within at least a portion of the end effector 1308 to open and close the jaws 1310, 1312. Where the member is an I-beam compression member, the member is configured to travel through slots formed in each jaw to pull the jaws into a parallel orientation and to compress tissue therebetween. The compression member can include a cutting element that can be integrally formed with the compression member or that can be a separate element. In some embodiments, the member can be a drive shaft that advances a sled through the end effector for firing staples from the end effector. In other embodiments, the member can be, or can be coupled to, a closure tube that advances to close opposed jaws of an end effector. Regardless of the specific configuration of the member 1400, it is coupled to the actuator 1314 such that the actuator 1314 is manually moved from the first position to the second position to cause the member 1400 to move proximally to thereby open the jaws 1310, 1312 of the end effector 1308.

If a cutting element is present, the cutting element is retracted proximally when the jaws are open.

Figure 14A:
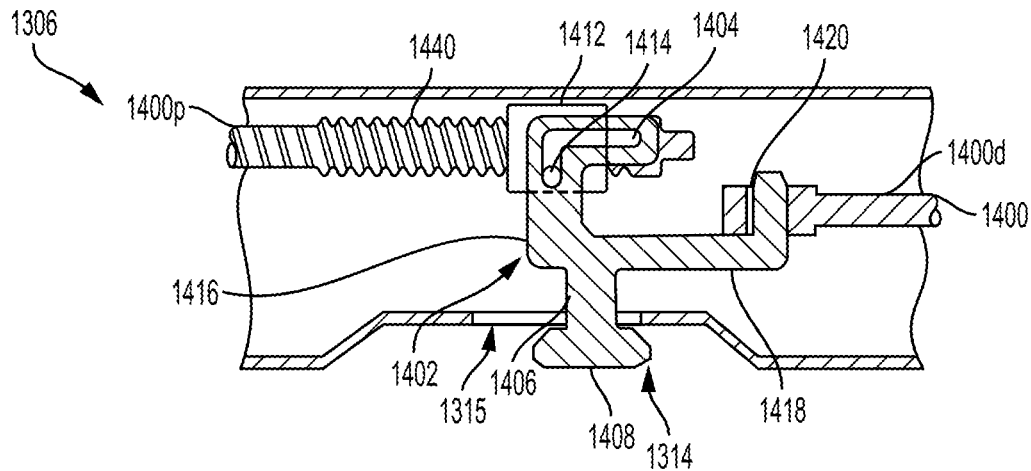
FIGS. 14A-14C illustrate an example of operation of a coupling mechanism configured to assist in opening and closing jaws of the end effector of FIG. 12.
Figure 14B:
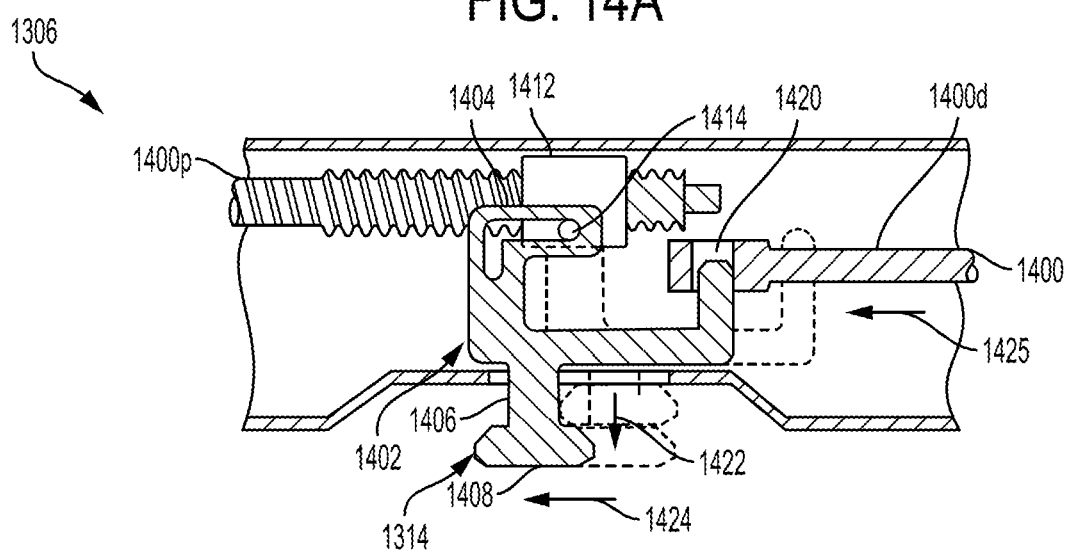
Figure 14C:
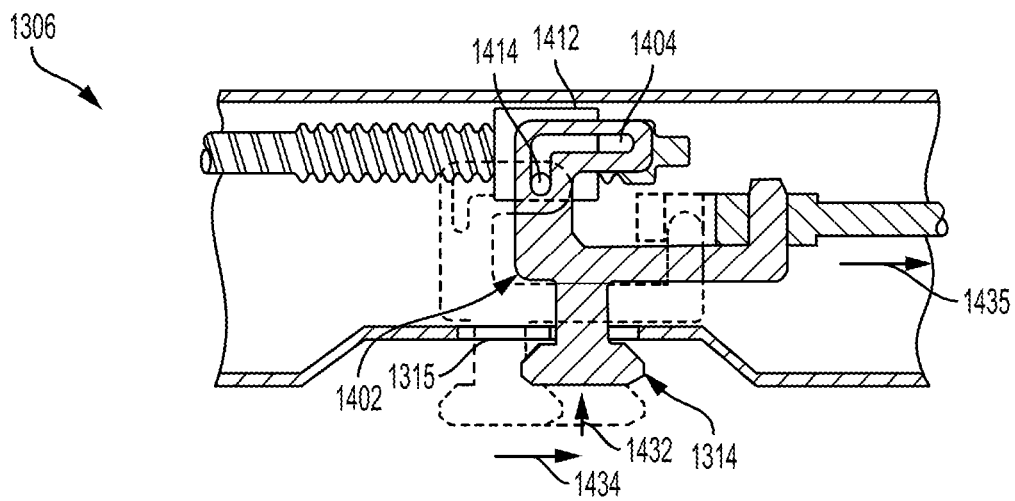

FIGS. 13A and 13B illustrate a portion of the surgical tool 1300 configured in accordance with the described techniques, and FIGS. 14A-14C illustrate an example of operation of a coupling mechanism that couples the actuator 1314 with the member 1400. As shown in FIG. 14A, the coupling mechanism is disposed within the elongate shaft 1306. In embodiments in which the elongate shaft 1306 includes the distal and proximal portions 1306d, 1306p, the coupling mechanism and the actuator 1314 can be disposed at the proximal portion 1306.

The coupling mechanism, shown in cross-section in FIGS. 14A-14B, is formed such that it is interposed between proximal and distal portions 1400p, 1400d of the member 1400 and such that it couples the proximal and distal portions 1400p, 1400d so that actuator 1314 can be used to manually override jaw opening/closing. As shown in FIGS. 14A-14C, the coupling mechanism includes a bracket 1402 having an L-shaped slot 1404, a worm gear 1410 formed on or coupled to the proximal portion 1400p and having a thread formed thereon, a nut 1412 within which worm gear 1410 is threaded, and a pin 1414 disposed on the nut 1412 and extending through the L-shaped slot 1404 of the bracket 1402. As shown, the bracket 1402 includes L-shaped proximal and distal legs 1416, 1418. The proximal leg 1416 has, in the knee and in the shorter portion of the "L," the L-shaped slot 1404 formed therein. The shorter portion of the "L" of the distal leg 1418 sits in an opening 1420 formed in the distal-most end of the distal portion 1400p of the member 1400.

The actuator 1314 can have many various configurations. For example, the actuator 1314 can be a lever, a tab, or any other feature coupled to a member configured to move proximally and distally to close and open end effector's jaws. In the example illustrated, the actuator 1314 extends from the proximal leg 1416 of the bracket 1402 as shown in FIG. 14A. The actuator 1314 can be formed integrally with the bracket 1402 or it can be a separate component attached to the bracket 1402 in a suitable way. The actuator 1314 is shaped such that it has a grip surface that can be manually engaged and moved in a convenient manner. For example, as shown in FIGS. 14A-14C, the actuator 1314 can be T-shaped such that it has a leg or stem 1406 and a head 1408 extending from the stem 1406. It should be appreciated, however, that the actuator 1314 can have other shapes, as the described techniques are not limited in this respect.

As shown in FIGS. 12, 13A, and FIGS. 14A-14C, the actuator 1314 is disposed on the elongate shaft 1306 such that the actuator 1314 can move within the slot 1315 formed in the shaft 1306. The jaws of the end effector (e.g., the end effector 1308 in FIG. 12, not shown in FIGS. 14A-14C) are coupled to the distal end of the shaft 1306. The portion 1400d of the member 1400 is coupled to the end effector such that, when the member 1400 is moved proximally and distally, the jaws of the end effector are caused to close and open, respectively.

FIG. 14A illustrates the actuator 1314 in the first position when the jaws of the end effector are closed. For example, FIG. 12 illustrates the end effector 1308 when its jaws 1310, 1312 are closed. In the first position, the actuator 1314 is disposed on the elongate shaft 1306 such that the actuator's stem 1406 is positioned within the slot 1315 and the head 1408 of the actuator 1314 protrudes above the outer surface of the shaft 1306. The shorter portion of the "L" of the distal leg 1418 sits in the opening 1420 in the member 1400.

When it is desired to open the jaws of the end effector 1308, the actuator 1314 can be manually moved from the first to the second position, as shown in FIG. 14B. For example, when the surgical tool is in the mode in which it is not deriving electrical power from the surgical robotic system and after the tool is retracted from the trocar, the actuator 1314 can be manually moved from the first to the second position to open the jaws 1310, 1312.

In the illustrated embodiment, the actuator 1314 can be pulled away from the shaft 1306, as shown by an arrow 1422 in FIG. 14B, and then moved proximally as shown by an arrow 1424 in FIG. 14B. FIG. 14B also illustrates in phantom lines the position of the bracket 1402 when the actuator 1314 is in the first position. These movements cause the L-shaped slot 1404 of the bracket 1402 to move about the pin 1414 such that the pin is seated within the opposite end of the L-slot's "L," as shown in FIG. 14B. The shorter portion of the "L" of the distal leg 1418 is moved in the opening 1420 in the direction shown by the arrow 1422 such that the distal leg 1418 is partially retracted from the opening. The actuator 1314 is moved proximally within the slot 1315 in the shaft 1306, as shown by an arrow 1425, thus causing the distal portion 1400d of the member 1400 to move proximally. This proximal movement of the member 1400 causes the jaws of the end effector 1308 to open. In this way, after the tool is retracted from the trocar with the end effector's jaws closed, the jaws can be opened by a user (e.g., a surgeon or other person) manually, despite the tool being disconnected from a power source. This then allows replacement of a staple cartridge assembly.

FIG. 13A shows the end effector 1308 with the jaws 1310, 1312 open by manually moving the actuator 1314 from the first to the second position, in the directions of the arrows 1422 and 1424. After the jaws of the end effector 1308 are opened, the removable and replaceable staple cartridge assembly 1311 can be removed from the first jaw 1310, as schematically shown in FIG. 13B. The end effector 1308 can thus be loaded with another removable and replaceable staple cartridge assembly. Furthermore, in some embodiments, the entire first jaw 1310 can be a removable and replaceable staple cartridge assembly removably coupled to the end effector in a suitable way. Thus, the entire first jaw 1310 can be removed and replaced with another removable and replaceable staple cartridge assembly.

After the staple cartridge assembly has been replaced, or at any other point when it is desirable to close the jaws of the end effector, the actuator 1314 can be returned from the second, "open-jaws," position to the first, "closed-jaws," position. FIG. 14C illustrates the actuator 1314 moved from the second to the first position, with the components of the coupling mechanism in the previous, second position, shown in phantom lines. As shown, the actuator 1314 is manually moved within the slot 1315 such that it is moved distally in the direction of an arrow 1434 and is then pushed towards the shaft 1306 as shown by an arrow 1432. Such movements of the actuator 1314 cause the member 1400 to move distally, in the direction show by an arrow 1435, which causes the jaws of the end effector to close.

After the jaws of the end effector are closed, the surgical tool can be placed in a mode (e.g., a "second mode") in which it is deriving electrical power from the surgical robotic system. For example, after the jaws are closed, the surgical tool can be inserted into a surgical access instrument to access a surgical site, and the surgical tool can be reconnected with the tool driver such that the tool can be operated as part of the surgical robotic system.

In some embodiments, techniques for controlling opening and closing of jaws of an end effector of a surgical tool of a surgical robotic system via a display disposed on a housing of the tool are provided. Such control can be performed when the surgical tool having the end effector at a distal end of its elongate instrument shaft thereof receives electrical power from a suitable power source. In this way, information, instructions, and any feedback related to operation of the surgical tool can be presented to a surgeon on the display. Also, the surgical tool's housing can include one or more controls configured to receive user input with respect to operation of the surgical tool. For example, the display can present an instruction to a user (in a textual and/or other format) that a staple cartridge assembly needs to be replaced, and a control of the one or more controls can accept user input in the form of an instruction to the surgical robotic system to open the jaws of the end effector. After the end effector's jaws are automatically opened in response to such instruction, the staple cartridge assembly supported by the end effector can be removed and the end effector can be reloaded with another staple cartridge assembly. The display can provide any other information related to operation of the surgical tool. Also, the one or more control can be configured to accept user input with respect to various other functions of the surgical tool.

Figure 15:
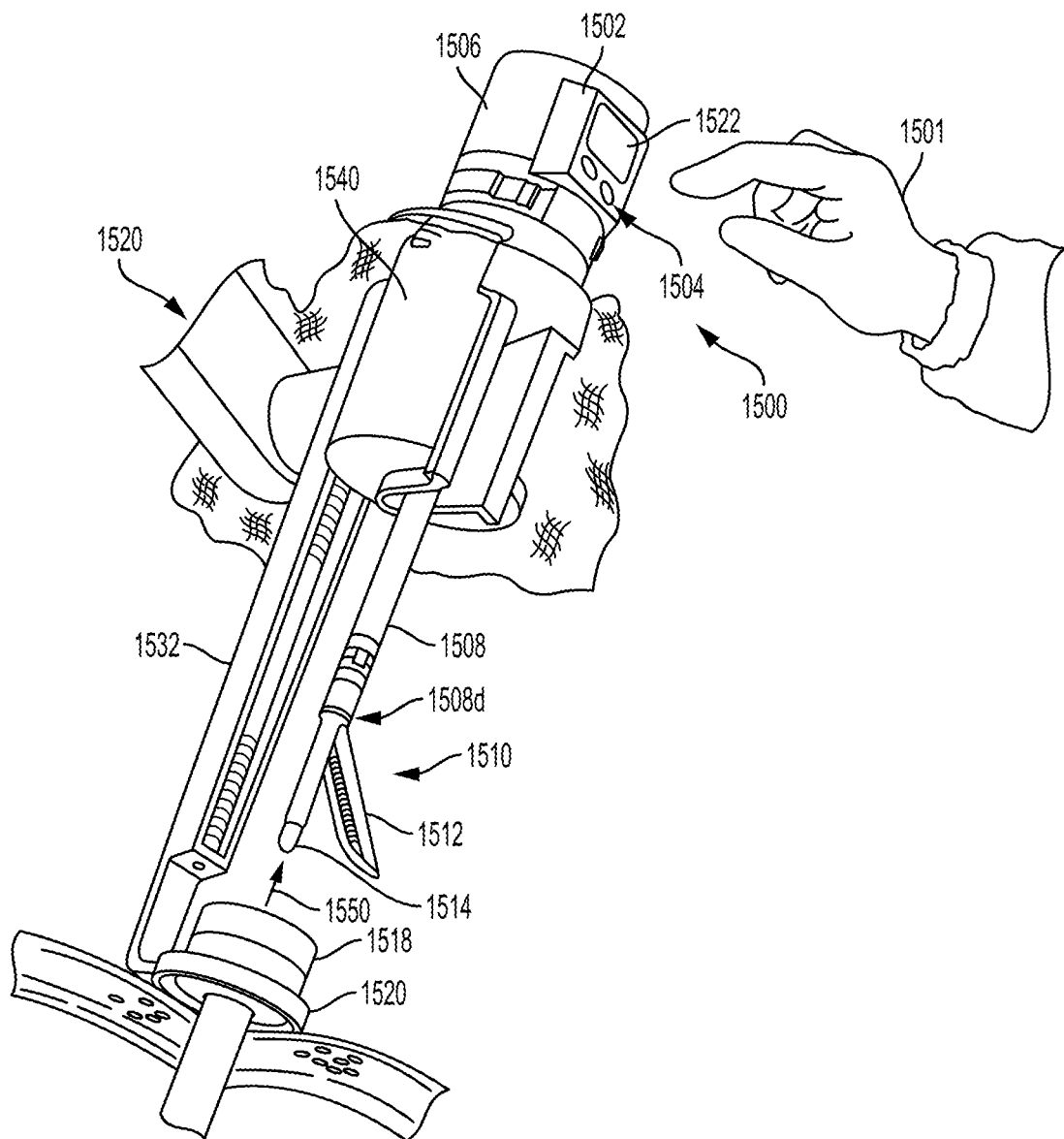
FIG. 15 is a perspective view of an embodiment of a surgical tool assembly in accordance with some embodiments.

FIG. 15 illustrates an example of a surgical tool assembly 1500 that includes a display 1502 and one or more controls 1504 in accordance with the described techniques. The surgical tool assembly 1500 can be part of any robotic surgical device and it can be similar, for example, to the surgical tool assembly 1130 shown in FIG. 11. Thus, as shown in FIG. 15, the surgical tool assembly 1500 is removably and replaceably attached to an electromechanical arm 1520 of a surgical robotic system that is capable of supplying electrical power to the surgical tool assembly 1500. The tool assembly 1500 is coupled to the electromechanical arm 1520 via a tool driver 1540. As shown, the tool assembly 1500 includes a housing 1506 having the display 1502 and the control(s) 1504, and an elongate shaft 1508 extending distally from the housing 1506 and having an end effector 1510 at a distal end 1508d thereof. The end effector 1510 has opposed first and second jaws 1512, 1514 that are movable between open and closed positions. At least one of the jaws, such as, in this example, the first jaw 1512, includes a removable and replaceable staple cartridge assembly 1516.

The surgical tool assembly 1500 can access a surgical site via a suitable surgical access instrument, an example of which is shown in FIG. 15 as a trocar 1518. Similar to the example of FIG. 11, the robotic arm 1520 can include a movable tool guide 1532 that can retract and extend relative to the tool driver 1540. The elongate shaft 1508 of the tool assembly 1500 can extend parallel to a shaft of the movable tool guide 1532 and can extend through a distal end feature 1520 (e.g., a ring or other feature) of the movable tool guide 1532 and into a patient. The trocar 1518 can be reversibly mated to the distal end feature 1520 such that the tool guide 1532 holds the trocar 1518 to allow the elongate shaft 1508 to be advanced through and retracted from the trocar 1518. It should be appreciated that the tool guide 1532 and the trocar 1518 are shown in FIG. 15 by way of example only, as these components can have any suitable configurations and the described techniques are not limited in this respect.

Figure 18:
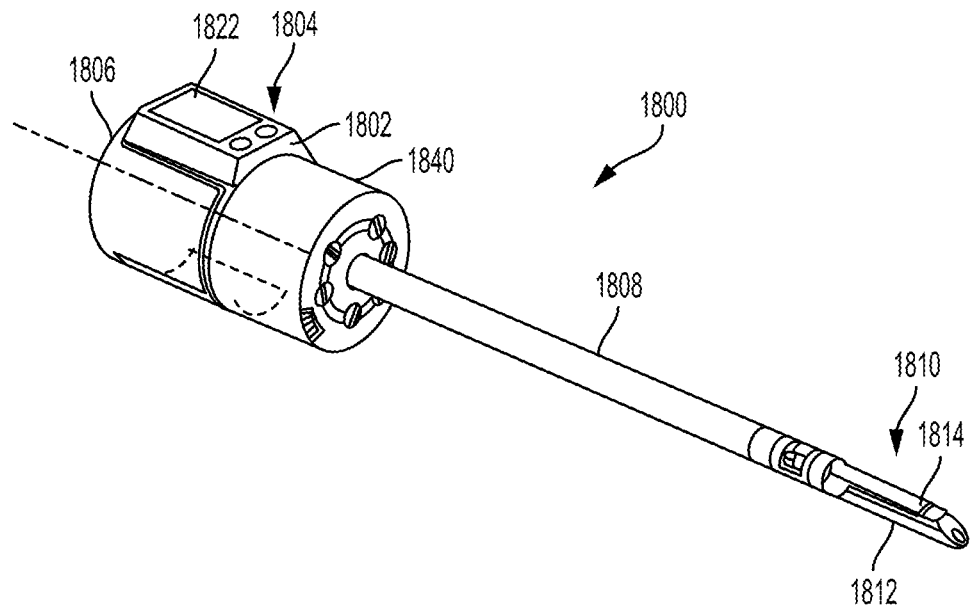
FIG. 18 is a perspective view of an embodiment of a surgical tool.
Figure 19:
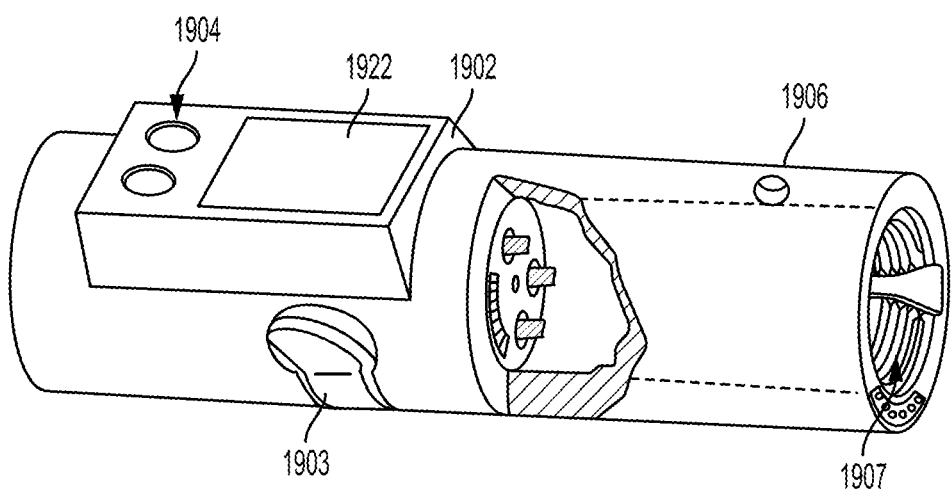
FIG. 19 is a perspective view of an embodiment of a housing of a surgical tool.

The housing 1506 of the surgical tool assembly 1500 can have a variety of different configurations. For example, the housing can be configured as shown in FIGS. 18 and 19 which are discussed in more detail below. The housing can be coupled to a tool driver and other components of the surgical robotic system in many different ways. Regardless of the specific configuration of the housing 1506, as mentioned above, it includes the display 1502 and one or more controls 1504.

The display 1502 can have a variety of different configurations and it can be of any suitable type. For example, the display 1502 (and/or its user interface) can be a liquid-crystal display (LCD), a light-emitting diodes (LED) display, or any other type of a display. The display can be shaped and sized such that it can present information thereon in a user-convenient manner. In the example illustrated in FIG. 15, the display 1502 can be formed on the housing 1506 such that an upper surface of the display 1502 is raised above the outer surface of the rest of the housing 1506. However, the display can have any other configuration. The display 1502 includes a user interface 1522 that can present information related to operation of the surgical tool assembly in textual and/or other formats. For example, the user interface 1522 can present information about an operational status of the surgical tool assembly 1500. The information can include indication(s) about a current operational status of components (e.g., the end effector) of the tool assembly, indication(s) (e.g., in the form of at least one instruction) about next steps to take, indication(s) about access control and any other type of information, as discussed in more detail below.

The one or more controls 1504 disposed on the housing 1506 can have any suitable configuration and they can be of any suitable type. The controls 1504 are configured to accept user input, which is shown in FIG. 15 by way of example only as a hand 1501. It should be appreciated that two controls 1504 are shown by way of example only, as the surgical tool assembly's housing can include one, three, or any other number of controls. The controls can be in the form of push buttons and/or other control elements (e.g., a lever, tab, switch, etc.). The controls can be part of the display, as in the example illustrated in FIG. 15. Additionally or alternatively, in some embodiments, the controls can be disposed on other portions of the housing 1506. Furthermore, the controls 1504 can be disposed above (e.g., as in FIG. 15), below, or on the side of the user interface 1522 of the display 1502, as the described techniques are not limited in this respect. In some embodiments, the display 1502 can be a touch screen display and the controls can be in the form of portions of the touch screen display.

The controls can vary in many different ways. For example, the controls can be pre-assigned specific functions such that a particular control is used to only accept user input to cause the surgical system to perform a certain function. In other embodiments, however, the same control can be used for more than one function, depending on one or more of an operational status of the surgical tool assembly, an operational status of the surgical system, and/or other factors. For example, when there is a need to receive certain input from a user, an indication indicating this need can be presented on the display, and one or more of the controls can be activated to receive respective user input. In some cases, the information presented on the display can indicate which control should be used to accept user input. Additionally, in some embodiments, one or more of the controls can be associated with a light indicator indicating a status of that control. For example, if user input is required to be received with respect to a control, the light indicator of that control can be red. Once the required used input is received (e.g., the button is pressed or other type of input is detected), the color of the control can change to green. It should be appreciated, however, that the controls can additionally or alternatively have any other features.

Regardless of their specific configurations, the controls include a control element configured to receive user input to cause the surgical tool assembly to be removed from a surgical access instrument. For example, with reference to components of FIG. 15, one of the controls 1504 can be a control configured to receive a user input that instructs the surgical robotic system to retract the surgical tool assembly 1500 from the trocar 1518, in the direction shown by an arrow 1550. In this way, the surgical tool assembly 1500 can be automatically retracted from the trocar 1518 when required, while the surgical tool assembly is receiving electrical power from surgical robotic system (e.g., via the tool driver 1540). The controls 1504 also include a control configured to accept user input comprising an instruction to the surgical robotic system to open jaws of an end effector coupled to the distal end of the tool's shaft (e.g., the end effector 1510 in FIG. 15 or any other end effector). The instruction to open the jaws can include an instruction to automatically disconnect a removable and replaceable staple cartridge assembly from the end effector. Accordingly, the described techniques allow the surgical robotic system to accept user input with respect to one of the controls 1504 to instruct the surgical robotic system to retract the tool with the end effector from the trocar, and to accept user input with respect to another of the controls 1504 to instruct the surgical robotic system to open the jaws of the end effector while the surgical tool assembly is receiving electrical power from surgical robotic system. In response to these inputs, the surgical robotic system automatically retracts the tool with the end effector from the trocar, opens the jaws of the end effector, and ejects the staple cartridge assembly from the tool.

The surgical robotic system can open the jaws of the end effector using any suitable mechanism. For example, the surgical tool assembly can include a member configured to move distally and proximally within at least a portion of the end effector to open and close the jaws. As described above in connection with FIGS. 11 and 12, the member can be an I-beam compression member, a drive shaft, a closure tube, or any other member configured to move distally and proximally within at least a portion of the end effector to open and close the end effector's jaws. Thus, regardless of the configuration of such member, the instruction to open the jaws that can be received by the surgical system via a control on the tool's housing can include an instruction to cause the member to automatically move proximally to thereby open the jaws. The member can be moved using any suitable mechanism. For example, motors in the tool driver can be operated to cause movement of the member.

It should be appreciated that, in some implementations, the surgical tool assembly includes an end effector that supports a staple cartridge assembly that is removable from a jaw of the end effector. In such implementations, after the surgical robotic system automatically opens the jaws of the end effector of the surgical tool assembly in response to receiving, via one or more controls, a respective user input, the staple cartridge assembly needs to be manually removed and replaced with another staple cartridge assembly.

It should also be appreciated that the controls on the housing of the surgical tool assembly can include any controls for accepting any suitable instructions related to operation of the surgical tool assembly. For example, one or more controls can be used to accept user input instructing the jaws of the end effector to close. As another example, one or more controls can be used to accept user input related to operation of the end effector during a surgical procedure. Any other controls can be used additionally or alternatively, including different types of controls that can be configured to receive used input in various manners.

Figures 16A, 16B:
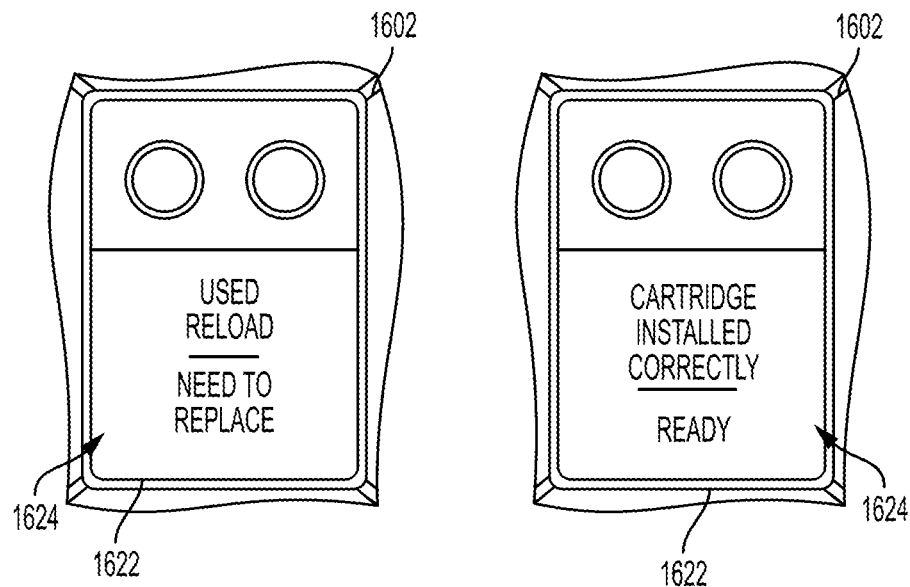
FIGS. 16A and 16B illustrate a display of the surgical tool assembly of FIG. 15.
Figure 17:
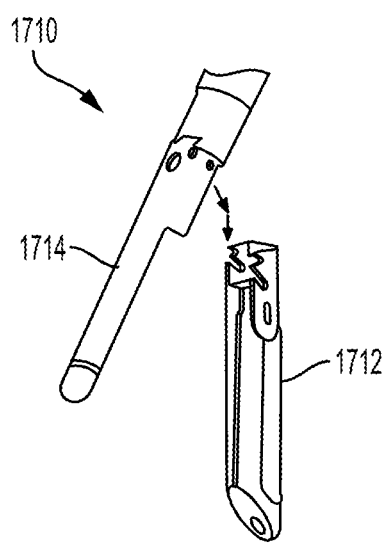
FIG. 17 illustrates an example of a removable and replaceable staple cartridge assembly of a surgical tool assembly.

Referring back to FIG. 15, the information presented on the user interface 1522 can include an indication that a staple cartridge assembly (e.g., the staple cartridge assembly 1516) must be replaced or reloaded. The surgical robotic system can determine in a suitable way (e.g., via suitable sensors) that the staple cartridge assembly of the end effector 1510 needs to be replaced, and the respective indication can be presented on the display 1502. For example, as shown in FIG. 16A by way of example only, a display 1602, which can be similar to the display 1502 in FIG. 15, can present, on a user interface 1622, an indication 1624 stating "Used Reload. Need to Replace." Such indication indicates that a staple cartridge assembly, referred to as a "reload," of an end effector of a surgical tool assembly must be replaced. The end effector can be configured such that the entire jaw supporting a staple cartridge assembly can be removable and replaceable. FIG. 17 illustrates an example of such an end effector 1710 having first and second opposed jaws 1712, 1714 configured to hold tissue therebetween. The first jaw 1712 is configured as a "reload"—a removable and replaceable staple cartridge assembly that can be removed as shown in FIG. 17 and replaced with another reload in the form of a removable and replaceable jaw carrying a staple cartridge assembly. It should be appreciated that the indication 1624 is only an example of a message that can be presented to a user via a display in accordance with the described techniques, as any other indication can provided to indicate that the staple cartridge assembly is required to be replaced.

Referring back to FIG. 15, when an indication, such as the indication 1624 shown in FIG. 16A or other indication, indicating that a staple cartridge assembly is required to be replaced is presented on the display, the one or more controls 1504 can be used to accept required user input. As discussed above, the controls 1504 can include a control element configured to accept user input to cause the surgical tool assembly to be removed from a surgical access instrument, and a control element configured to accept user input to cause the jaws of the end effector to open. These controls can be used to accept user input when the display presents the indication indicating that a staple cartridge assembly is required to be replaced.

Referring back to FIG. 15, the information presented on the display 1502 can include an indication that the staple cartridge assembly has been removed from the end effector 1510 when the staple cartridge assembly is absent from the end effector 1510. The surgical robotic system can determine in a suitable way (e.g., via suitable sensors) that the staple cartridge assembly is absent from the end effector 1510 and the respective indication can be presented on the display 1502. The information that the staple cartridge assembly has been removed from the end effector can be presented after the staple cartridge assembly has been removed (e.g., automatically ejected as discussed above or removed manually) and before the tool has been loaded with another staple cartridge assembly. After the tool has been loaded with another staple cartridge assembly (which may be done as respective loading instructions are presented on the display 1502), the display 1502 can present feedback information indicating whether the staple cartridge assembly has been installed correctly or incorrectly. For example, as shown in FIG. 16B by way of example only, the user interface 1622 of the display 1602 can present a message stating "Cartridge Installed Correctly. Ready," indicating that the staple cartridge assembly has been installed correctly and that the surgical tool assembly can be used (i.e., is "ready") for a surgical procedure. Like in the example of FIG. 16A, any other message can be displayed to indicate a status of the installation of the staple cartridge assembly, including a message that the staple cartridge assembly has been installed incorrectly if this is determined to be the case. Any other feedback information can be presented additionally or alternatively.

Any other information can be presented on the display 1502 on FIG. 15, the display 1602 of FIGS. 16A and 16B, or any other display in accordance with the described techniques. For example, the information can include instructions for reloading the end effector, such as, e.g., steps for removing and replacing a staple cartridge assembly either in the form of an assembly seated by a jaw or in the form of a jaw removable and replaceable as a reloading unit. Additionally or alternatively, the information can include instructions for operating the surgical tool assembly, which can be presented at any time during a time when the surgical tool assembly is in use. More than one indication can be displayed on the display at the same time. The information presented on the display can be in a textual, visual, a combination thereof, or in any other format. In addition, in some embodiments, the housing can additionally be configured to provide indication(s) in audio format.

In some embodiments, the information presented on the display of the housing of the surgical tool assembly can include instructions for resolving at least one error in operation of the end effector. For example, in embodiments in which the surgical tool assembly includes one or more bailout mechanisms for retracting an actuator on a surgical tool when a failure is encountered, the display can present instructions on how to perform the bailout process using the bailout mechanisms(s). In some embodiments, the information presented on the display of the surgical tool assembly can include indications and instructions on how to resolve an improperly attached modular shaft of a surgical tool, and/or other indications and instructions related to operation and "hot-swapping" of modular shafts.

The display and controls on a housing of a surgical tool assembly in accordance with the described techniques can be included in a variety of different surgical tool assemblies. FIGS. 18 and 19 illustrate examples of surgical tools assemblies that can include a display and control in accordance with the described techniques. FIG. 18 illustrates a portion of a surgical tool assembly 1800 having a housing 1806, a tool driver 1840, and an elongate shaft 1808 extending distally from the housing 1806 and having an end effector 1810 at a distal end thereof. The housing 1806 and the tool driver 1840 can be coupled to one another in any suitable way. The end effector 1810 has opposed first and second jaws 1812, 1814, with the first jaw 1812 having a removable and replaceable staple cartridge assembly. The housing 1806 includes a display 1802 that can have a user interface 1822 and one or more controls 1804. The display 1802 and the controls 1804 can be similar to the display 1502 and the controls 1504 in FIG. 15, respectively. The elongate shaft 1808 can be an attachable modular shaft. When multiple modular shafts can be used with the same housing, the surgical tool assembly can further include an adapter (not shown), e.g., as described in the above-referenced applications.

FIG. 19 illustrates a portion of a surgical tool assembly 1900 having a tool housing 1906 including a display 1902 that can have a user interface 1922 and one or more controls 1904. The tool housing 1906 can be configured to receive a surgical tool (not shown) in a channel 1907 of the housing. The tool housing 1906 can have a bailout mechanism 1903, as shown in FIG. 19. In embodiments in which the surgical tool assembly includes one or more bailout mechanisms, the display 1902 can present (e.g., on the user interface 1922) information related to using the bailout mechanism(s). Furthermore, any other information related to operation of the surgical tool assembly can be presented, as discussed above. The controls 1904, which allow accepting user instructions with respect to various aspects of operation of the surgical tool assembly, can be configured similar to the controls 1504 in FIG. 15, or in any other manner.

In embodiments described above, a removable and replaceable staple cartridge assembly supported by at least one of jaws of an end effector coupled to an elongate instrument shaft of a surgical tool assembly can be replaced manually. In some embodiments, however, a surgical robotic system can automatically replace the staple cartridge assembly with another removable and replaceable staple cartridge assembly. Furthermore, the jaws can be prepared for accepting another removable and replaceable staple cartridge assembly. The preparation process can include, for example, cleaning the jaws (e.g., from unused staples that can be stuck in the cartridge and/or from any dirt, debris, etc.) and drying the cleaned jaws. Also, in embodiments in which one or both jaws removably hold a buttress, after the end effector is loaded with a new removable and replaceable staple cartridge assembly, the end effector can be loaded with a buttress. The end effector with the buttress can then be inspected to ensure proper positioning of the buttress on the jaw(s) of the end effector.

FIGS. 20-23 illustrate exemplary processes involved in replacing a removable and replaceable staple cartridge assembly supported by an end effector with a new removable and replaceable staple cartridge assembly effector. The processed can be performed using an automated reloading system, a cleaning/drying station, and/or any other systems, as described in more detail below.

Figure 20:
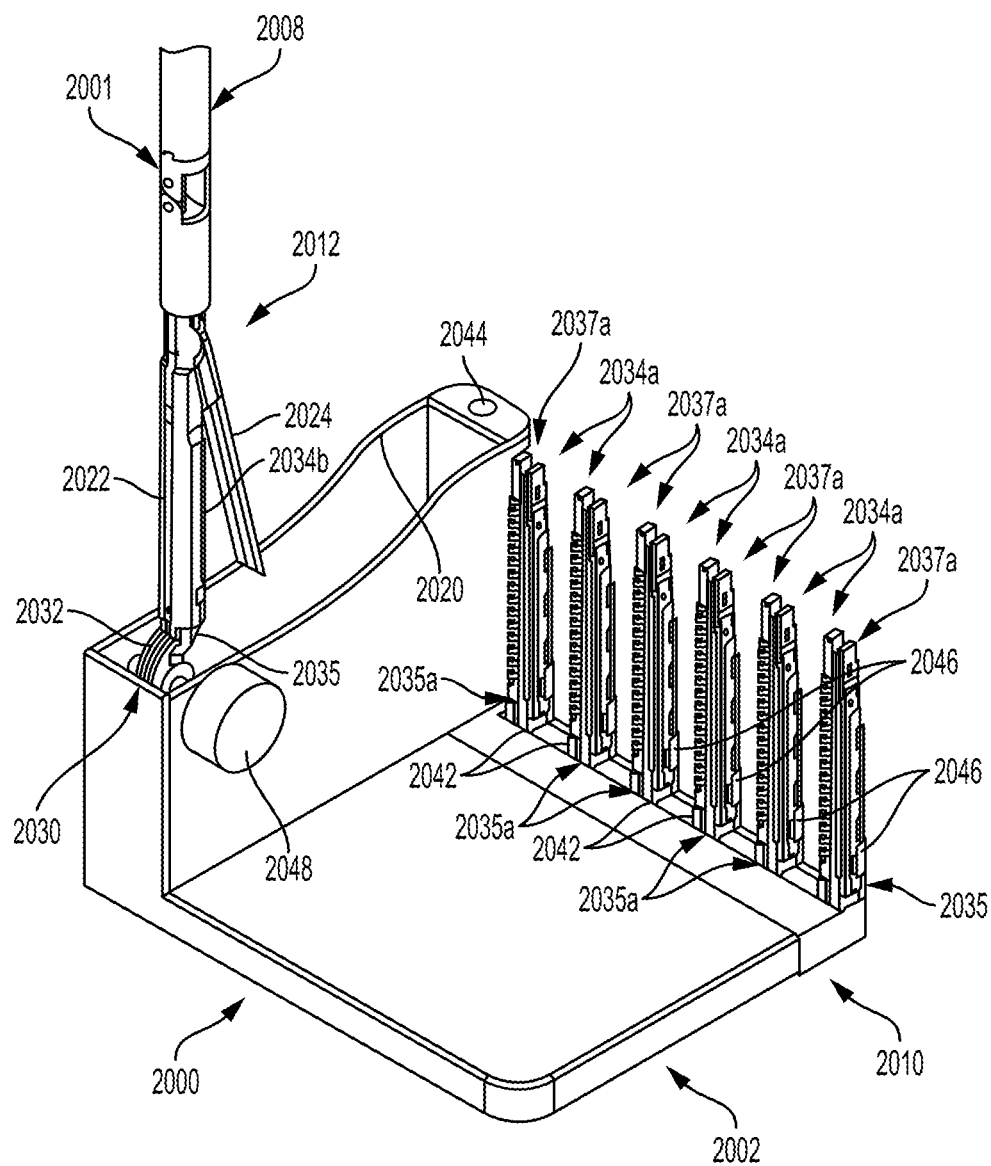
FIG. 20 illustrates an example of a staple cartridge reloading station.

FIG. 20 illustrates an example of an automated reloading system 2000 that can be used to reload an end effector. The automated reloading system 2000 is similar to an automated reloading system described in U.S. Pat. No. 8,931,682, entitled "Robotically-Controlled Shaft Based Rotary Drive Systems for Surgical Instruments," issued on Jan. 13, 2015, the content of which is incorporated herein by reference in its entirety. The automated reloading system 2000 is configured to replace a "spent" surgical end effector component in a manipulatable surgical tool assembly 2001 of a surgical robotic system with a "new" surgical end effector component. The manipulatable surgical tool assembly 2001 can be, for example, the surgical tool assembly 1300 (FIG. 12), the surgical tool assembly 1500 (FIG. 15), or any other surgical tool assembly. The end effector is coupled to a distal end of an elongate shaft 2008 of the surgical tool assembly 2001. As used herein, the term "surgical end effector component" may include, for example, a surgical staple cartridge, a disposable loading unit or other end effector components that, when used, are spent and must be replaced with a new component. Furthermore, the term "spent" means that the end effector component has been activated and is no longer useable for its intended purpose in its present state. For example, in the context of a surgical staple cartridge or disposable loading unit, the term "spent" means that at least some of the unformed staples that were previously supported therein have been "fired" therefrom. As used herein, the term "new" surgical end effector component refers to an end effector component that is in condition for its intended use. In the context of a surgical staple cartridge or disposable loading unit, for example, the term "new" refers to such a component that has unformed staples therein and which is otherwise ready for use.

As shown in FIG. 20, the automated reloading system 2000 includes a base portion 2002. The base portion 2002 includes a new component support section or arrangement 2010 that is configured to operably support at least one new surgical end effector component in a "loading orientation." As used herein, the term "loading orientation" means that the new end effector component is supported in such away so as to permit the corresponding component support portion of the surgical tool assembly to be brought into loading engagement with (i.e., operably seated or operably attached to) the new end effector component (or the new end effector component to be brought into loading engagement with the corresponding component support portion of the surgical tool assembly) without human intervention beyond that which may be necessary to actuate the robotic system. However, in some cases, at least one new surgical end effector component can be loaded manually, or based at least in part on manual manipulations by a surgical nurse or other medical personnel.

A surgical end effector that can be reloaded using the described systems and methods can have any suitable configurations. In the example shown in FIG. 20, the surgical end effector 2012 includes an anvil 2024, and an elongated channel 2022 configured to operably seat a staple cartridge 2034*b*. It should be appreciated, however, that the elongated channel is shown by way of example only, as the described techniques can be used for reloading of an end effector including any component support portion configured to operably seat a staple cartridge.

For explanation purposes, new (unused) cartridges are designated herein as "2034*a*" and a spent cartridge is designated as "2034*b*," as in FIG. 20. In some embodiments, the cartridges 2034*a*, 2034*b* can be configured to be retained through a snap fit engagement (i.e., loading engagement) within the channel 2022 of a surgical end effector 2012. However, as a person skilled in the art will appreciate, the described automated cartridge reloading system 2000 can be effectively employed in connection with the automated removal and installation of other cartridge arrangements.

In the "loading orientation," a distal tip portion 2035*a* of the a new surgical staple cartridge 2034*a* is inserted into a corresponding support cavity 2042 in the new cartridge support section 2010 such that a proximal end portion 2037*a* of the new surgical staple cartridge 2034*a* is located in a convenient orientation for enabling a suitable component of the surgical robotic system to manipulate the surgical end effector 2012 into a position wherein the new cartridge 2034*a* can be automatically loaded into the channel 2022 of the surgical end effector 2012. In some embodiments, the base 2002 includes at least one sensor 2044 which communicates with a control system of a robotic controller of a suitable control system, such as the control system 315 of the user-side portion 311 of FIG. 1.

As shown in FIG. 20, the base 2002 further includes a collection receptacle 2020 that is configured to collect spent cartridges 2034*b* that have been removed or disengaged from the surgical end effector 2012 that is operably attached to the surgical robotic system. In addition, in one form, the automated reloading system 2000 includes an extraction system 2030 for automatically removing the spent end effector component from the corresponding support portion of the end effector or manipulatable surgical tool assembly without specific human intervention beyond that which may be necessary to activate the surgical robotic system.

In some embodiments, the extraction system 2030 includes an extraction member 2032. In one form, for example, the extraction member 2032 is rigidly supported on the base portion 2002. The extraction member can have one or more suitable features (e.g., a hook or other feature, not shown in FIG. 20) configured to engage the distal end 2035 of a spent cartridge 2034*b* when it is supported in the elongated channel 2022 of the surgical end effector 2012. In various forms, the extraction member 2032 is conveniently located within a portion of the collection receptacle 2020 such that when the spent end effector component (cartridge 2034*b*) is brought into extractive engagement with the extraction member 2032, the spent end effector component (cartridge 2034*b*) is dislodged from the corresponding component support portion (elongated channel 2022), and falls into the collection receptacle 2020. Thus, the manipulatable surgical tool assembly manipulates the end effector attached thereto to bring the distal end 2035 of the spent cartridge 2034*b* therein into engagement with a suitable feature of the extraction member 2032 and then moves the end effector in such a way to dislodge the spent cartridge 2034*b* from the elongated channel 2022. It should be appreciated that the extraction member 2032 can have any other configuration. For example, it can be coupled to an extraction motor 2048 that is controlled by the controller of surgical robotic system.

In some embodiments, a sensor arrangement can be located adjacent to the extraction member 2032. The sensor arrangement can comprise a sensor that is configured to sense the presence of the surgical end effector 2012 and, more particularly the tip 2035*b* of the spent surgical staple cartridge 2034*b* thereof as the distal tip portion 2035*b* is brought into engagement with the extraction member 2032. In some embodiments, the sensor arrangement can comprise, for example, a light curtain arrangement. However, other forms of proximity sensors can be employed additionally or alternatively. In such arrangement, when the surgical end effector 2012 with the spent surgical staple cartridge 2034*b* is brought into extractive engagement with the extraction member 2032, the sensor senses the distal tip 2035*b* of the surgical staple cartridge 2034*b* (e.g., the light curtain is broken). When the extraction member 2032 removes the surgical staple cartridge 2034*b* and the cartridge 2034*b* falls into the collection receptacle 2020, the light curtain is again unbroken. A person skilled in the art will appreciate that any other sensor arrangements can also be employed to provide the robotic controller with an indication that the spent surgical staple cartridge 2034*b* has been removed from the surgical end effector 2012.

After the spent surgical staple cartridge 2034*b* has been removed from the surgical end effector 2012, the surgical end effector 2012 can be positioned to grasp a new surgical staple cartridge 2034*a* between the channel 2022 and the anvil 2024. As shown in FIG. 20, each cavity 2042 has a corresponding upstanding pressure pad 2046 associated with it. The surgical end effector 2012 can be positioned such that the pressure pad 2046 is located between the new cartridge 2034*a* and the anvil 2024. Once in that position, the robotic system causes the anvil 2024 to close onto the pressure pad 2046, which serves to push the new cartridge 2034*a* into snapping engagement with the channel 2022 of the surgical end effector 2012. Once the new cartridge 2034*a* has been snapped into position within the elongated channel 2022, the robotic system then withdraws the surgical end effector 2012 from the automated cartridge reloading system 2000 for use in connection with performing another surgical procedure.

Figure 21:
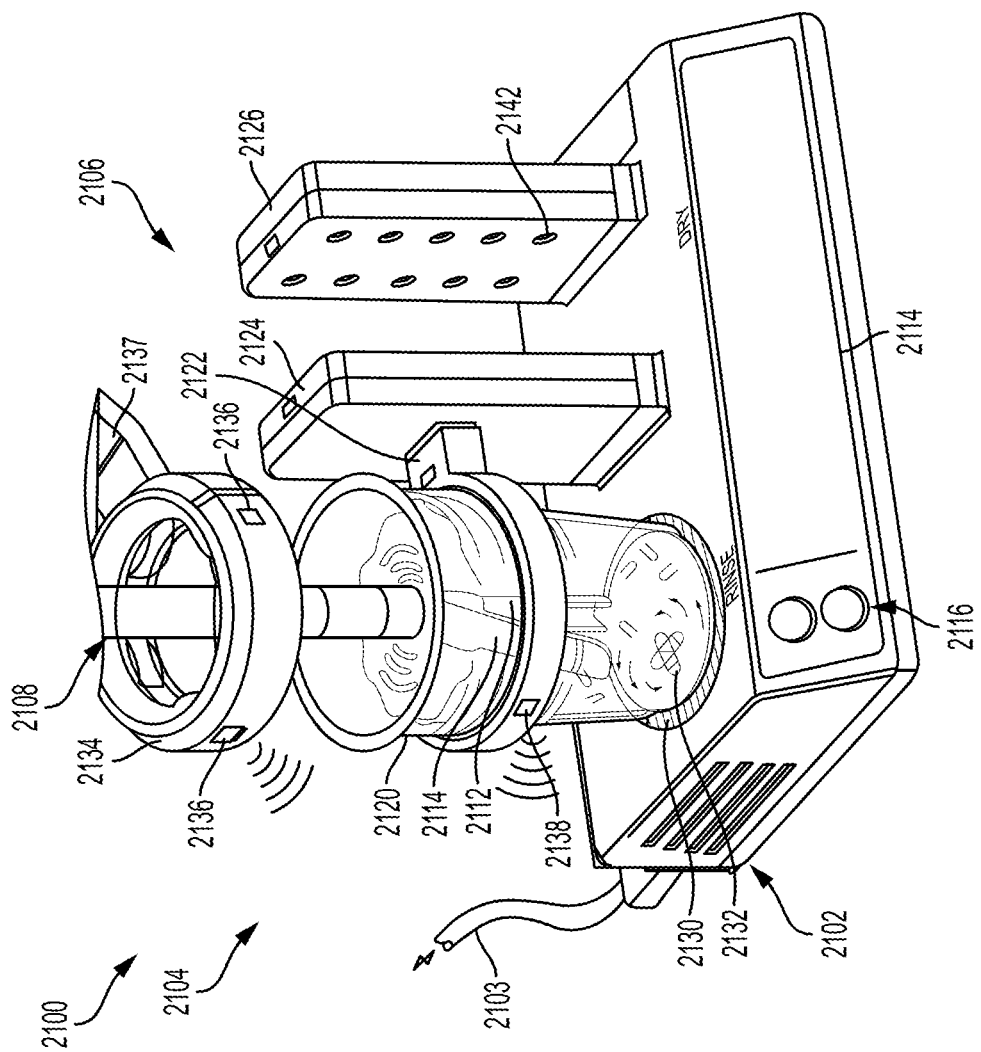
FIG. 21 illustrates an example of a cleaning and drying station, showing the end effector of FIG. 20 being processed at a cleaning portion of the cleaning and drying station.

It should be appreciated that the automated cartridge reloading system 2000 is shown in FIG. 20 by way of example only, as automated cartridge reloading systems having other configurations can be used. Furthermore, in some embodiments, after a spent surgical staple cartridge (e.g., the spent surgical staple cartridge 2034*b* in FIG. 20) has been removed from an end effector (e.g., the end effector 2012), the surgical system can cause the surgical end effector to be moved to a cleaning and drying station. An example of such cleaning and drying station 2100 is shown in FIG. 21. The cleaning and drying station 2100 can be controlled via a controller of the surgical robotic system, e.g., the control system 315 in FIG. 1, or any other control controller(s).

As shown in FIG. 21, the cleaning and drying station 2100, which is configured to be connected to a power source via a wired connector 2103, includes a base portion 2102 supporting thereon a cleaning portion or station 2104 and a drying portion or station 2106. The base portion 2102 also includes a display 2114 configured to display information related to operating status of the base portion 2102, such as information related to cleaning or drying jaws of an end effector. The display 2114 can include, or it can be associated, with one or more controls (e.g., buttons) 2116 that are configured to accept user instructions with respect to operation of the cleaning and drying station 2100.

As further shown in FIG. 21, the cleaning station 2104 includes a bracket 2118 configured to removably hold a generally cylindrical container 2120 (e.g., a cap or other container). The bracket 2118 is coupled, via an arm 2122, to a first panel 2124 of the drying station 2106, as also shown in FIG. 21. However, it should be appreciated that the container 2120, which can have various shapes, can be coupled to the base portion 2102 in any other way. The container 2120 is configured to hold therein a cleaning solution, such as, for example, a saline solution, or any other cleaning solution). In some embodiments, the base portion 2102 in proximity to the container 2120 can include one or more sensors configured to sense amount of fluid in the container 2120. For example, FIG. 21 shows by way of example a circular pressure sensor 2130 configure to sense amount of fluid in the container 2120. When it is determined that the amount of fluid in the container 2120 is not sufficient or excessive, the controller can cause the display 2114 to display a respective indication, or it can be indicated in other manner that the amount of fluid in the container 2120 is above or below a required level.

Furthermore, the part of the base portion 2102 that forms the cleaning station 2104 includes one or more electromagnets (not shown) disposed in the area underneath the container 2120, and the container 2120 includes a stirring element 2132, such as a magnet. The electromagnets create a rotating magnetic field that causes the stirring element 2132 immersed in the solution disposed in the container 2120 to spin, thus stirring the solution.

An end effector operatively coupled to a shaft of a surgical tool assembly of the surgical robotic system (e.g., the end effector 2012 shown in FIG. 20, or any other end effector), can be brought to the cleaning station 2104 after the staple cartridge assembly has been removed from the end effector, as in the example of FIG. 20. FIG. 21 illustrates an end effector 2110 coupled to a shaft 2108 and having first and second jaws 2112, 2114. At least one of the jaws (in this example, the first jaw 2112) is configured to replaceably seat a staple cartridge assembly. The surgical tool assembly having the end effector 2110 at a distal end of the shaft 2108 can be coupled to an electromechanical arm of the surgical robotic system, and the cleaning of the end effector 2110, as well as the subsequent drying, can be performed automatically. As shown in FIG. 21, the shaft 2108 having the end effector 2110 coupled thereto has a trocar holding ring 2134 of a movable tool guide disposed therearound. The trocar holding ring 2134 can be similar, for example, to the distal end feature or ring 1133 of the movable tool guide 1130 shown in FIG. 11. The trocar holding ring 2134, configured to engage with a trocar, can be part of a trocar holding member, a portion (e.g., arm) 2137 of which is shown in FIG. 21. The trocar holding member can be disengaged from the trocar for any number of reasons, including, as in this example, for replacing a staple cartridge assembly.

The cleaning station 2104 can be configured to communicate wirelessly with one or more components of the surgical robotic system. In this example, the trocar holding ring 2134 can include one or more sensors 2136 (e.g., Hall sensors or other proximity sensors) configured to communicate with one or more sensors 2138 (e.g., Hall sensors or other proximity sensors) disposed on the container 2120. In this way, the cleaning station 2104 can determine, based on the information sensed by the sensors 2138, that the shaft 2108 with the end effector 2110 is inserted into the container 2120, using the trocar holding ring's sensors 2136. It should be appreciated that two sensors 2136 on the trocar holding ring 2134 and one sensor 2138 disposed on the container 2120 are shown by way of example only, as any number of sensors of a suitable type can be employed. Also, although the sensor 2138 is shown to be disposed adjacent a rim of the container 2120, it should be appreciated that one or more sensors 2138 can be disposed at other locations on the container 2120, or at other locations at the cleaning station 2104.

In use, the end effector 2110 is manipulated such that its jaws 2112, 2114 are open using any of the techniques described above, and the end effector 2110 coupled to the shaft 2108 is immersed into the cleaning solution in the container 2120. The cleaning station 2104 will then be activated, manually (e.g., via the control(s) 2116) and/or automatically, to perform cleaning of the end effector 2110. The stirring element 2132 immersed in the solution in the container 2120 is agitated and the solution thus swished is stirred to help clean the end effector 2110. In this way, the cleaning station 2104 is used to get rid of unformed surgical staples that could have remained in the support portion (e.g., a channel) of the jaw 2012, and to clean the jaw 2012 from dirt and other impurities in preparation for a new staple cartridge assembly.

The processing at the cleaning station 2104 can be performed for a certain duration of time, which can be monitored automatically or based on user input using a timer, including a timer build-in into the cleaning, based on an instruction received via the one or more controls 2116, or in any other manner. The display 2114 can display information related to the cleaning process, including the timing information. In some embodiments, the display 2114 can be a touch-screen display that can be configured to receive user input setting a time of the cleaning process.

Figure 22:
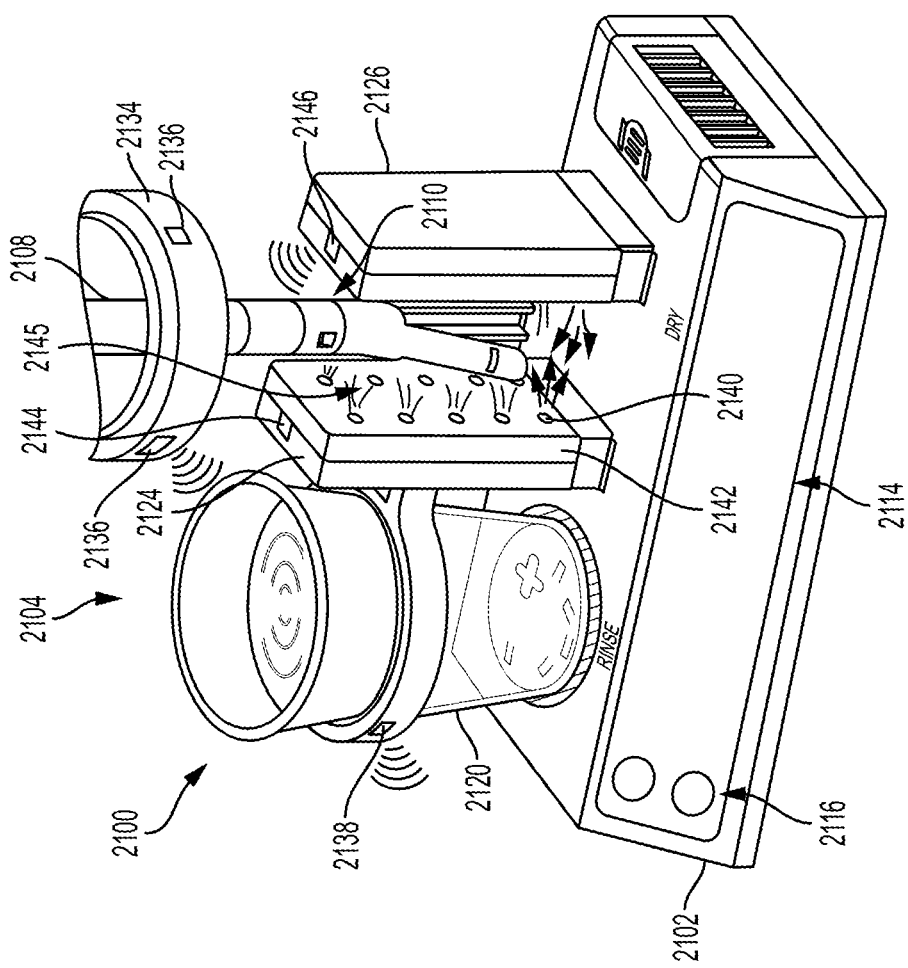
FIG. 22 illustrates the cleaning and drying station of FIG. 21, showing the end effector of FIG. 21 being processed at a drying portion of the cleaning and drying station.

After the processing at the cleaning station 2104 is determined to be complete, the shaft 2108 with the end effector 2110 can be transported to the drying station 2106. As shown in FIG. 22, the base 2102 at the drying station 2106 can have an air intake component 2143 with an air filter inside (not shown). The drying station 2106 can include a fan and a heater (not shown). Regardless of the specific components and their configuration, the drying station 2106 is configured to provide hot air. For example, as shown in FIG. 22, the end effector can be placed between the first and second panels 2124, 2126 of the drying station 2106 that each are configured to expel hot air, schematically shown as 2145, from its side facing another panel. The first and second panels 2124, 2126 can have sensors 2144, 2146 (e.g., Hall sensors or other proximity sensors) configured to communicate with the sensors 2136 on the trocar holding ring 2134 to detect presence of the end effector 2110 in proximity to the panels 2124, 2126. This detection can activate the drying station 2106 to perform the drying process. Additionally or alternatively, the drying process can be controlled via one or more of the controls 2116. FIG. 22 shows schematically that multiple openings, one of which is labeled as 2140, on the side 2142 of the first panel 2124 blow hot air onto the end effector 2110 placed between the first and second panels 2124, 2126. In this example, the side 2142 of the first panel 2124 has ten openings 2140, although any other number of the openings can be formed, or the first panel 2124 can have other features configured to expel hot air in the direction of the second panel 2126. The second panel 2126 can have similar ten openings 2142 (as shown in FIG. 21), or any other features to expel hot air in the direction of the first panel 2124. The panels 2124, 2126 can be configured in the same or different ways to dry an end effector placed therebetween. In addition, it should be appreciated that the first and second panels 2124, 2126 can have other shapes and configurations.

Similar to the cleaning process, the drying can be performed for a predetermined period of time which can be set automatically or in any other manner. For example, the control(s) 2116 can be used to receive input with respect to setting the time of the drying. The display 2114 can display information related to a progress of the drying process (e.g., a time remaining), or it can display any other information.

Figure 23:
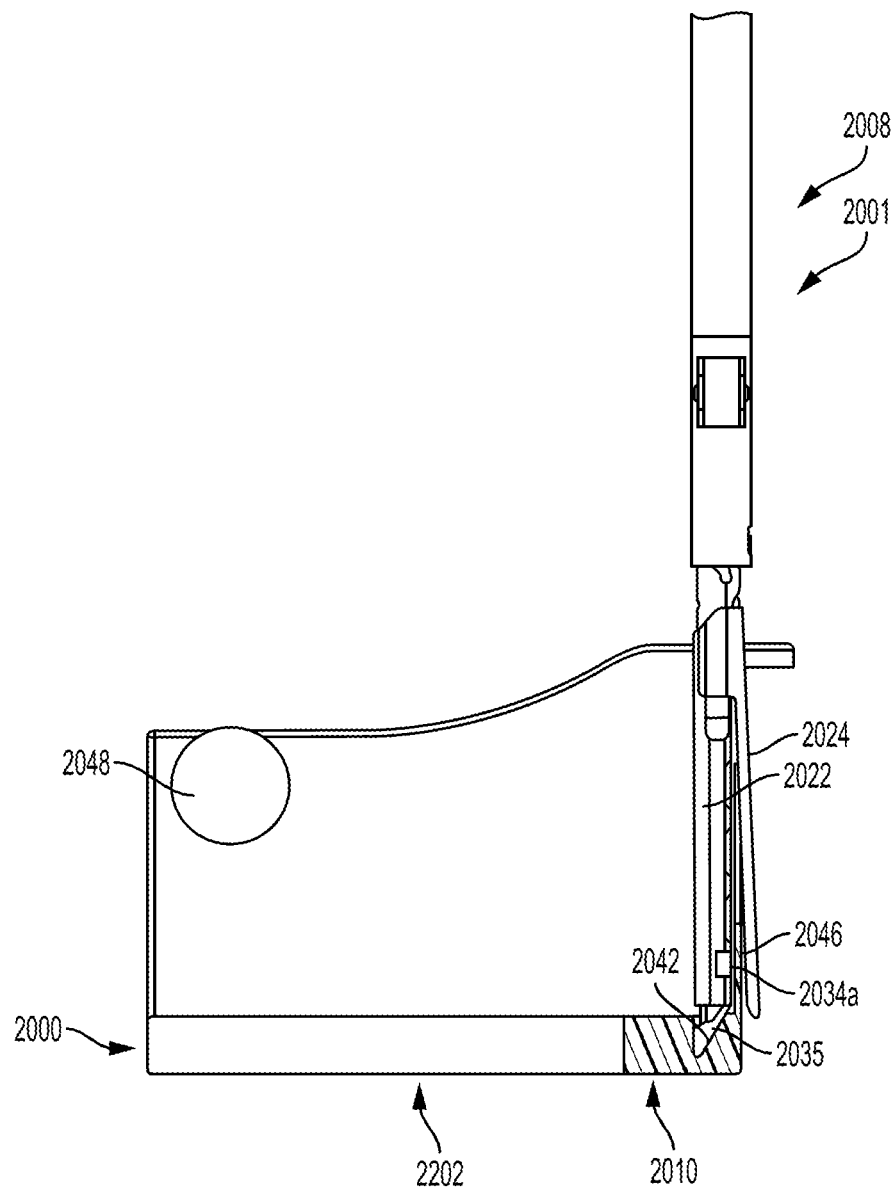
FIG. 23 illustrates the end effector of FIG. 22 being loaded with a new staple cartridge assembly using the staple cartridge reloading station of FIG. 20.

After it is determined that the process of drying the end effector 2110 is completed, the end effector 2110 can be loaded with a new staple cartridge assembly. FIG. 23, which illustrates a cross-sectional view of the surgical tool assembly 2001 of FIG. 20, illustrates schematically the new staple cartridge assembly loading process. Components of FIG. 23 are described above in connection with FIG. 20 and are therefore not described in detail in conjunction with FIG. 23. As shown in FIG. 23, the end effector 2012 is positioned to grasp a new surgical staple cartridge 2034a between the channel 2022 and the anvil 2024. Specifically, each cavity 2042 has a corresponding upstanding pressure pad 2046 associated with it. The surgical end effector 2012 is located such that the pressure pad 2046 is located between the new cartridge 2034a and the anvil 2024. Once in that position, the surgical robotic system closes the anvil 2024 onto the pressure pad 2046 which serves to push the new cartridge 2034a into snapping engagement with the channel 2022 of the surgical end effector 2012. Once the new cartridge 2034a has been snapped into position within the elongated channel 2022, the robotic system then withdraws the surgical end effector 2012 from the automated cartridge reloading system 2000 for use in connection with performing another surgical procedure.

In some embodiments, at least one of the jaws of an end effector coupled to a shaft of a surgical tool assembly operably coupled to a robotic surgical system can be associated with a buttress. The buttress can be used for a variety of purposes, including for hemostasis, for promoting healing of a wound at the surgical site, and/or for multiple other purposes. If the buttress is to be loaded on one or both jaws of the end effector prior to deployment of the end effector during a surgical procedure, the end effector can be moved to a buttress loading station.

Figure 24:
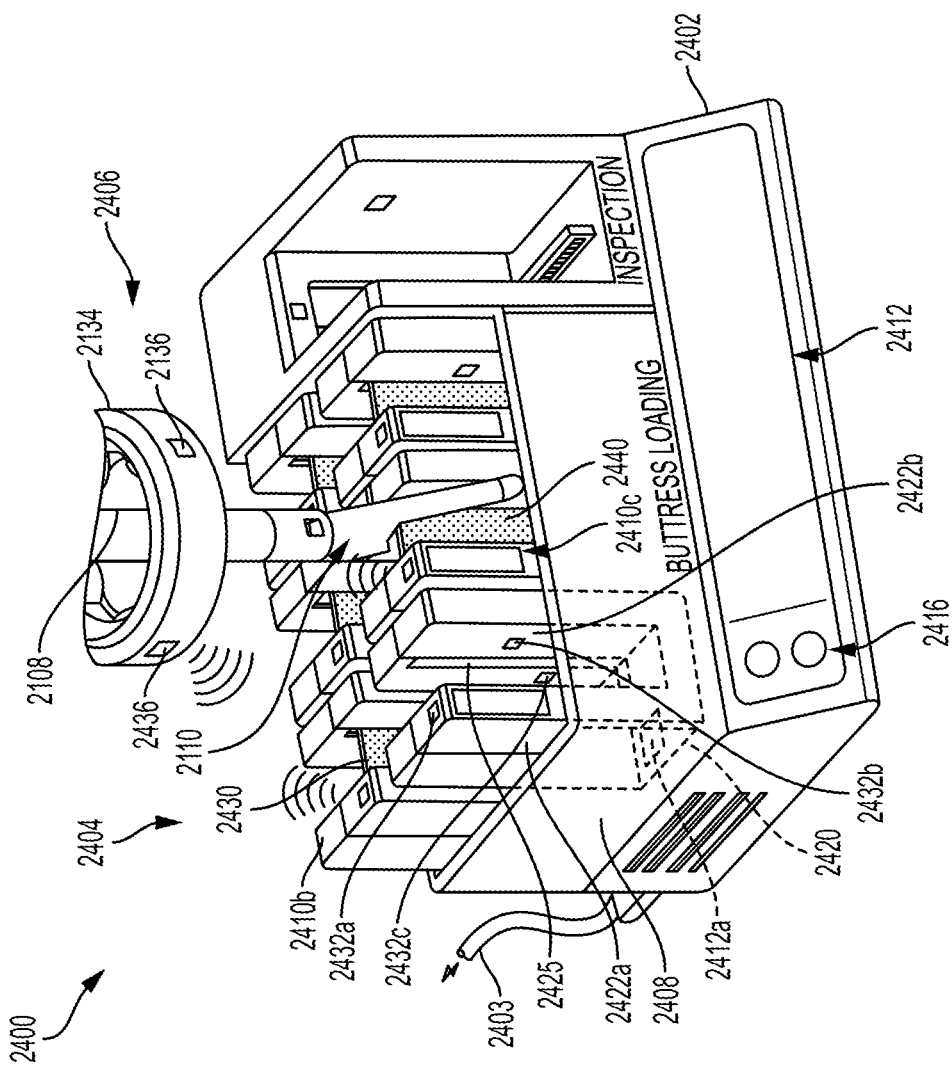
FIG. 24 illustrates an example of a buttress loading station, showing the end effector of FIG. 23 being loaded with a buttress at a buttress loading portion of the buttress loading station.
Figure 25:
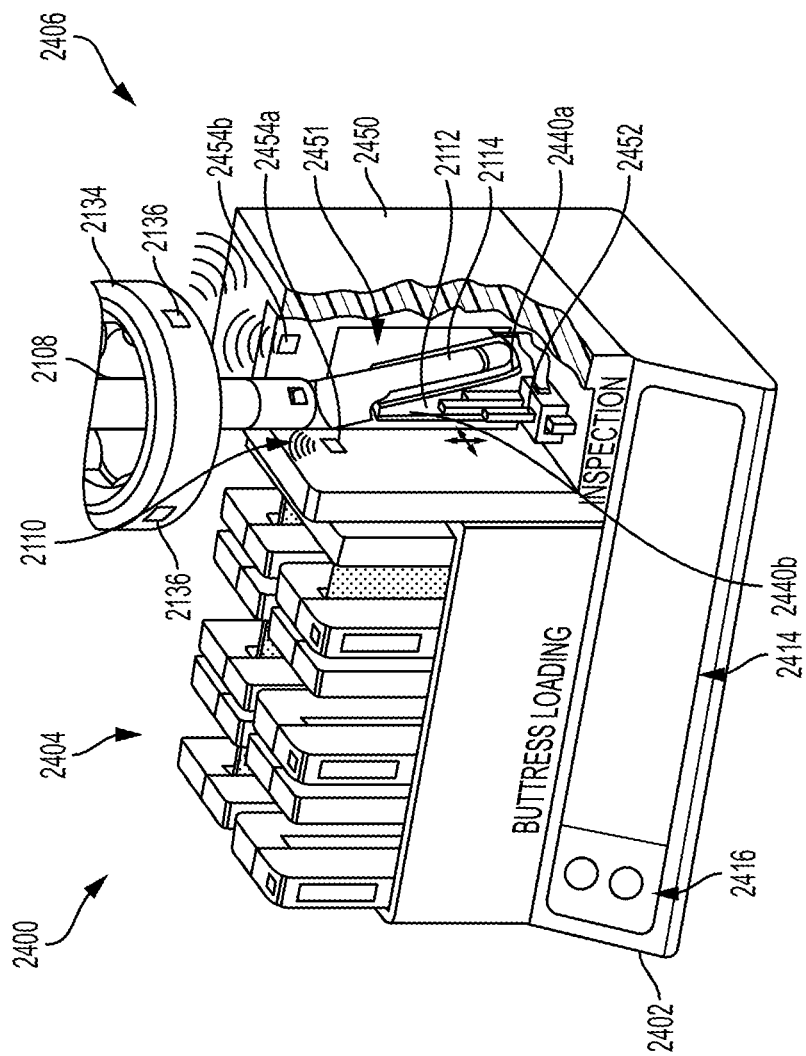
FIG. 25 illustrates the end effector of FIG. 24 with the buttress loaded thereon, being inspected at a buttress inspection portion of the buttress loading station.

FIGS. 24 and 25 illustrate an example of a buttress loading station 2400 that can be used to load an end effector with a buttress and to then verify whether the buttress has been properly placed. As shown in FIGS. 24 and 25, the buttress loading station 2400, which is configured to be connected to a power source via a wired connector 2403, includes a base portion 2402 having a display 2414 (e.g., an LCD or any other type of a display), and one or more controls 2416. The buttress loading station 2400 includes a buttress loading portion 2404 and a buttress inspection portion 2406, as also shown in FIGS. 24 and 25. The loading portion 2404 includes a cartridge holder 2408 having a plurality of buttress reload cartridges, two of which are labeled as buttress cartridges 2410a, 2410b. Other buttress cartridges have the same or similar configurations and features. In this example, the cartridge holder 2408 includes six buttress cartridges. It should be appreciated, however, that the cartridge holder can removably hold any other number of buttress cartridges, such as less or greater than six.

In the example illustrated, each buttress cartridge is shaped as an inverted "U," with the straight edges between the base and arms of the "U." For example, as shown for the buttress cartridge 2410a, each of the buttress cartridges includes a base 2420 and arms 2422a, 2422b extending from opposite sides of the base. The arms 2422a, 2422b can have a buttress removably held therebetween. For example, the buttress can be held within slots 2425 formed on inner walls of the arms 2422a, 2422b of the buttress cartridge buttress cartridge 2410a. In FIG. 24, the buttress cartridge 2410a is shown without the buttress, indicating that the buttress has been removed to be placed onto a jaw of the end effector, as discussed below. The buttress cartridge 2410b, similar to the rest of the buttress cartridges in the holder 2408, is shown to have a buttress 2430 held between its arm.

Each of the buttress cartridges can include a sensor configured to communicate with the buttress loading station 2400. Thus, in FIG. 24, the buttress cartridge 2410a is shown to include at least one sensor 2412a (e.g., a Hall sensor or any other suitable type of a sensor) configured to communicate with one or more sensors associated with the buttress loading station 2400. In this way, the buttress loading station 2400 can detect presence of buttress cartridges. Also, it can keep track of how many "unused" (i.e., having their buttress intact) and "used" (i.e., without buttresses) buttress cartridges are held by the holder 2408. A type of the buttresses can also be sensed. This can be done additionally using other sensors disposed on the buttress cartridges, such as three sensors 2432a, 2432b, 2432c (e.g., Hall sensors or any other suitable type of sensors) on the buttress cartridge 2410a. It should be appreciated that the buttress cartridge can include other number of sensors (e.g., two or greater than three).

In use, as illustrated in FIG. 24, an end effector, such as the end effector 2110 coupled to the distal end of the shaft 2108 and also shown in FIGS. 20-22, is brought to the buttress loading portion 2404 of the buttress loading station 2400 and placed such that its jaws have a buttress 2440 removably held by the buttress cartridge 2410c therebetween. The jaws are then caused to close and engage the buttress 2440 such that the buttress 2440 becomes attached to the jaws of the end effector 2110. Thus, as shown in FIG. 25, the buttress 2440 becomes attached to both channel 2112 having the staple cartridge assembly loaded therein and the anvil 2114 of the end effector 2110.

The one of more sensors 2136 on the trocar holding ring 2134 of the movable tool guide that is disposed around the shaft 2108 can communicate with the sensors disposed on the buttress cartridge 2410c (which can be the same or similar sensors to the sensors 2432a, 2432b, 2432c on the buttress cartridge 2410a). In this way, the surgical robotic system can communicate wirelessly with the buttress loading station 2400 to exchange suitable information. Also, a relative position of the shaft 2108 with the end effector 2110 with respect to the buttress cartridge can be sensed. Furthermore, the sensors 2136 on the trocar holding ring 2134 can communicate wirelessly with the buttress loading station 2400 via suitable sensors on the station and/or other sensor(s) on the buttress (e.g., a sensor similar to the sensor 2412a on the buttress cartridge 2410a) to sense a status of the buttress cartridge and any other features.

The display 2414 can display information related to a status of the buttress currently in use (being loaded), a type of that buttress, and any other information. The controls 2416 can be used to control operation of the buttress loading station 2400.

The described techniques can thus be used to engage the end effector with one or more piece of buttress to releasably attach the buttress to the end effector. The buttress can be attached to one or both of the cartridge body and the anvil of the end effector. The buttress can be configured to be attached to one or both jaws of the end effector using a pressure sensitive adhesive material disposed on one or both sides of the buttress. Thus, as in this example, where the buttress can attach to both jaws and is thus formed of two separate portions each being attached to a respective jaw, both portions of the buttress facing the jaw's opposed surfaces can have a pressure sensitive adhesive material disposed thereon. Thus, when the jaws of the end effector are closed upon the buttress disposed on the buttress cartridge such that pressure is applied to the buttress, the buttress becomes attached to the jaws. The entire buttress material carried by the buttress cartridge can be transferred onto the end effector, as in the example illustrated in FIGS. 24 and 25. Alternatively, a portion of the buttress material can be attached to the jaw(s) of the end effector.

The buttress can be formed from any suitable materials. For example, it can be formed from any absorbable polymer, such as, e.g., VICRYL®, or any other. The buttress can releasably incorporate therein various drugs and/or healing agents.

Once the end effector is loaded with the buttress, it can be moved from the buttress loading portion 2404 to the buttress inspection portion 2406. Referring to FIG. 25, after the end effector 2110 has been loaded with the buttress 2440 as described above, such that the cartridge body 2112 includes a buttress portion 2440a and the anvil 2114 includes a buttress portion 2440b, it can be transported to the buttress inspection portion 2406 of the buttress loading station. The buttress inspection portion 2406 determines whether the buttress 2440 has been attached to the end effector's jaw properly. As shown in FIG. 25, the buttress inspection portion 2406 includes a compartment 2450 configured to removably seat an end effector therein. The compartment 2450, shown partially in cross-section in FIG. 25, can be generally rectangular and configured to accept the end effector into a cavity 2451 formed therein, from the top. It should be appreciated, however, that the compartment 2450 can have any other configurations. The compartment 2450 can include two or more sensors 2454a, 2454b (e.g., Hall or other types) configured to communicate with the sensors 2136 on the trocar holding member 2134 such that the buttress inspection portion 2406 communicates with the surgical robotic system having the end effector 2110 operatively coupled thereto. The sensors 2454a, 2454b are also used to determine a proper positioning of the end effector 2100 within the compartment 2450.

The buttress inspection portion 2406 can inspect a buttress attached to one or both jaws of the end effector in a number of different ways. In this example, the compartment 2450 houses one or more cameras 2452 configured to swipe across the surfaces of the jaws 2112, 2114 to determine whether the buttress portions 2440a, 2440b are placed correctly on the jaws. Specifically, the camera 2452 can detect exposed anvil pockets and exposed cartridge pockets, and thus detect whether some areas of the surface of the end effector's jaws are not properly covered. The detection information, as well as any other information related to the status of the newly loaded buttress 2440, can be displayed on the display 2414. This information can also be communicated to the controller of the surgical robotic system. If it is determined that the buttress has not been attached properly to the jaw(s), the surgical robotic system can be notified accordingly and appropriate measures can be taken.

As discussed above, the controls 2416 can be used to operate the buttress inspection portion 2406 and its components, such as the camera 2452, or any other components. The display 2414 can communicate with a controller of the surgical robotic system and can indicate to the system when the end effector 2100 having the staple cartridge and the buttress is ready to be used for a surgical procedure.

In should be appreciated that an end effector can be processed at the cleaning and drying station 2100 and the buttress loading station 2500 automatically, such that a robotic arm to which a surgical tool having the end effector is coupled can bring the shaft with the end effector to the stations 2100, 2500. Also, in some embodiments, some of the operations of the preparation of the end effector for use in a surgical procedure can be manual. For example, in embodiments where the shaft is modular, such shaft with an end effector can be manually brought to one or both the stations to prepare the end effector for surgical procedure.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A robotic surgical device, comprising:
   a surgical tool assembly configured to be removably and replaceably attached to an electromechanical arm of a surgical robotic system that is capable of supplying electrical power to the surgical tool assembly, the surgical tool assembly having
   a housing,
   an elongate shaft extending distally from the housing and having an end effector at a distal end thereof, the end effector having opposed jaws that are movable between open and closed positions with at least one of the jaws comprising a removable and replaceable staple cartridge assembly,
   a display on the housing, the display having an interface configured to present user information related to operation of the surgical tool assembly, and
   one or more controls formed on the housing and configured to accept user input comprising at least one instruction to the surgical robotic system, the at least one instruction comprising an instruction to open the jaws, the one or more controls configured to correspond to an indicated input need presented on the display.

2. The robotic surgical device of claim 1, wherein the surgical tool assembly comprises a member configured to move distally and proximally within at least a portion of the end effector to open and close the jaws, the instruction to open the jaws comprises an instruction to cause the member to automatically move proximally to thereby open the jaws.

3. The robotic surgical device of claim 1, wherein the at least one instruction comprises an instruction to cause the surgical tool assembly to be removed from a surgical access instrument.

4. The robotic surgical device of claim 1, wherein the one or more controls comprise at least one button.

5. The robotic surgical device of claim 1, wherein the information comprises information about an operational status of the surgical tool assembly.

6. The robotic surgical device of claim 5, wherein the information comprises an indication that the staple cartridge assembly has been removed from the end effector when the staple cartridge assembly is absent from the end effector.

7. The robotic surgical device of claim 5, wherein the information comprises at least one of an indication that the cartridge assembly is required to be replaced, an indication of whether the cartridge assembly has been installed correctly or incorrectly, instructions for reloading the end effector, instructions for operating the surgical tool assembly, and instructions for resolving at least one error in operation of the end effector.

8. The robotic surgical device of claim 1, wherein the at least one of the jaws is the replaceable and removable staple cartridge assembly and the at least one instruction to the surgical robotic system comprises an instruction to remove the at least one of the jaws from the end effector.

9. The robotic surgical device of claim 1, wherein the interface comprises a touch screen interface.

10. The robotic surgical device of claim 1, wherein the elongate shaft comprises a proximal portion and a distal portion having the end effector, the distal portion being removably and replaceably coupled to the proximal portion.

* * * * *